United States Patent
Walberg et al.

(10) Patent No.: US 9,872,724 B2
(45) Date of Patent: Jan. 23, 2018

(54) APPARATUS FOR TISSUE CUTTING AND SEALING

(71) Applicant: Aesculap AG, Tuttlingen (DE)

(72) Inventors: Erik Walberg, Palo Alto, CA (US); Brandon Loudermilk, Palo Alto, CA (US)

(73) Assignee: AESCULAP AG (DE)

( * ) Notice: Subject to any disclaimer, the term of this patent is extended or adjusted under 35 U.S.C. 154(b) by 369 days.

(21) Appl. No.: 14/430,948

(22) PCT Filed: Sep. 26, 2013

(86) PCT No.: PCT/IB2013/002133
§ 371 (c)(1),
(2) Date: Mar. 25, 2015

(87) PCT Pub. No.: WO2014/049423
PCT Pub. Date: Apr. 3, 2014

(65) Prior Publication Data
US 2015/0250528 A1    Sep. 10, 2015

Related U.S. Application Data

(60) Provisional application No. 61/705,721, filed on Sep. 26, 2012.

(51) Int. Cl.
*A61B 18/18* (2006.01)
*A61B 18/14* (2006.01)
(Continued)

(52) U.S. Cl.
CPC .. *A61B 18/1445* (2013.01); *A61B 2018/0063* (2013.01); *A61B 2018/00184* (2013.01);
(Continued)

(58) Field of Classification Search
CPC ...... A61B 18/1445; A61B 2018/00601; A61B 2018/00309; A61B 2018/0063;
(Continued)

(56) References Cited

U.S. PATENT DOCUMENTS 3,356,408 A    12/1967  Stutz
3,527,224 A    9/1970   Rabinowitz
(Continued)

FOREIGN PATENT DOCUMENTS

CA    2061215    2/1992
CA    2833530    11/2008
(Continued)

OTHER PUBLICATIONS

Chinese Office Action dated Aug. 30, 2016 for Chinese Application No. 201380055342.7, including English translation, 19 pages.
(Continued)

*Primary Examiner* — Mallika D Fairchild
(74) *Attorney, Agent, or Firm* — RatnerPrestia

(57) ABSTRACT

An electrosurgical device for cutting and sealing tissue includes an upper jaw located at a distal end of the electrosurgical device that opposes a lower jaw. The lower jaw is pivotally connected to the upper jaw by a pivot connection. The pivot connection includes a passage that contains a portion of the upper jaw. The upper jaw is axially displaceable through the passage to pivot the upper jaw relative to the lower jaw between a relatively open condition and a relatively closed condition. The upper jaw and lower jaw are operable in the relatively closed condition to deliver RF energy to tissue.

31 Claims, 9 Drawing Sheets

(51) Int. Cl.
   *A61B 18/00* (2006.01)
   *A61B 90/00* (2016.01)
(52) U.S. Cl.
   CPC .............. *A61B 2018/00202* (2013.01); *A61B 2018/00309* (2013.01); *A61B 2018/00601* (2013.01); *A61B 2090/035* (2016.02)
(58) Field of Classification Search
   CPC ........... A61B 2018/00202; A61B 2018/00184; A61B 2090/035
   See application file for complete search history.

(56) References Cited

U.S. PATENT DOCUMENTS

| | | |
|---|---|---|
| 3,709,215 A | 1/1973 | Richmond |
| 3,742,955 A | 7/1973 | Battista |
| 3,845,771 A | 11/1974 | Vise |
| 3,920,021 A | 11/1975 | Hiltebrandt |
| 3,970,088 A | 7/1976 | Morrison |
| 4,018,230 A | 4/1977 | Ochiai |
| 4,041,952 A | 8/1977 | Morrison, Jr. |
| 4,072,153 A | 2/1978 | Swartz |
| 4,094,320 A | 6/1978 | Newton |
| 4,231,372 A | 11/1980 | Newton |
| 4,492,231 A | 1/1985 | Auth |
| 4,532,924 A | 8/1985 | Auth |
| 4,590,934 A | 5/1986 | Malis |
| 4,671,274 A | 6/1987 | Sorochenko |
| 4,972,846 A | 11/1990 | Owens |
| 4,976,717 A | 12/1990 | Boyle |
| 4,979,948 A | 12/1990 | Geddes |
| 4,998,527 A | 3/1991 | Meyer |
| 5,037,379 A | 8/1991 | Clayman |
| 5,041,101 A | 8/1991 | Seder |
| 5,059,782 A | 10/1991 | Fukuyama |
| 5,078,736 A | 1/1992 | Behl |
| 5,108,408 A | 4/1992 | Lally |
| 5,133,713 A | 7/1992 | Huang |
| 5,151,102 A | 9/1992 | Kamiyama |
| 5,156,613 A | 10/1992 | Sawyer |
| 5,178,618 A | 1/1993 | Kandarpa |
| 5,190,541 A | 3/1993 | Abele |
| 5,207,691 A | 5/1993 | Nardella |
| 5,217,030 A | 6/1993 | Yoon |
| 5,234,425 A | 8/1993 | Fogarty |
| 5,250,074 A | 10/1993 | Wilk |
| 5,267,998 A | 12/1993 | Hagen |
| 5,269,780 A | 12/1993 | Roos |
| 5,269,782 A | 12/1993 | Sutter |
| 5,273,524 A | 12/1993 | Fox |
| 5,277,201 A | 1/1994 | Stern |
| 5,281,216 A | 1/1994 | Klicek |
| 5,282,799 A | 2/1994 | Rydell |
| 5,290,287 A | 3/1994 | Boebel |
| 5,295,990 A | 3/1994 | Levin |
| 5,300,068 A | 4/1994 | Rosar |
| 5,300,087 A | 4/1994 | Knoepfler |
| 5,312,023 A | 5/1994 | Green |
| 5,324,289 A | 6/1994 | Eggers |
| 5,326,013 A | 7/1994 | Green |
| 5,330,471 A | 7/1994 | Eggers |
| 5,330,502 A | 7/1994 | Hassler |
| 5,336,229 A | 8/1994 | Noda |
| 5,336,237 A | 8/1994 | Chin |
| 5,341,807 A | 8/1994 | Nardella |
| 5,342,381 A | 8/1994 | Tidemand |
| 5,352,223 A | 10/1994 | McBrayer |
| 5,352,235 A | 10/1994 | Koros |
| 5,354,336 A | 10/1994 | Kelman |
| 5,356,408 A | 10/1994 | Rydell |
| 5,374,277 A | 12/1994 | Hassler |
| 5,377,415 A | 1/1995 | Gibson |
| 5,391,166 A | 2/1995 | Eggers |
| 5,395,369 A | 3/1995 | McBrayer |
| 5,396,900 A | 3/1995 | Slater |
| 5,397,320 A | 3/1995 | Essig |
| 5,403,312 A | 4/1995 | Yates |
| 5,405,344 A | 4/1995 | Williamson |
| 5,417,687 A | 5/1995 | Nardella |
| 5,423,814 A | 6/1995 | Zhu |
| 5,431,676 A | 7/1995 | Dubrul |
| 5,438,302 A | 8/1995 | Goble |
| 5,443,463 A | 8/1995 | Stern |
| 5,443,470 A | 8/1995 | Stern |
| 5,445,638 A | 8/1995 | Rydell |
| 5,447,513 A | 9/1995 | Davison |
| 5,449,355 A | 9/1995 | Rhum |
| 5,456,684 A | 10/1995 | Schmidt |
| 5,458,598 A | 10/1995 | Feinberg |
| 5,462,546 A | 10/1995 | Rydell |
| 5,472,442 A | 12/1995 | Klicek |
| 5,478,003 A | 12/1995 | Green |
| 5,480,399 A | 1/1996 | Hebborn |
| 5,482,054 A | 1/1996 | Slater |
| 5,484,435 A | 1/1996 | Fleenor |
| 5,484,436 A | 1/1996 | Eggers |
| 5,496,312 A | 3/1996 | Klicek |
| 5,496,317 A | 3/1996 | Goble |
| 5,514,134 A | 5/1996 | Rydell |
| 5,520,698 A | 5/1996 | Koh |
| 5,531,744 A | 7/1996 | Nardella |
| 5,540,684 A | 7/1996 | Hassler, Jr. |
| 5,540,685 A | 7/1996 | Parins |
| 5,542,945 A | 8/1996 | Fritzsch |
| 5,549,606 A | 8/1996 | McBrayer |
| 5,549,637 A | 8/1996 | Crainich |
| 5,556,397 A | 9/1996 | Long |
| 5,558,100 A | 9/1996 | Cox |
| 5,558,671 A | 9/1996 | Yates |
| 5,562,700 A | 10/1996 | Huitema |
| 5,562,701 A | 10/1996 | Huitema |
| 5,562,702 A | 10/1996 | Huitema |
| 5,562,720 A | 10/1996 | Stern |
| 5,564,615 A | 10/1996 | Bishop |
| 5,569,243 A | 10/1996 | Kortenbach |
| 5,571,100 A | 11/1996 | Goble |
| 5,573,535 A | 11/1996 | Viklund |
| 5,578,052 A | 11/1996 | Koros |
| 5,599,350 A | 2/1997 | Schulze |
| 5,601,224 A | 2/1997 | Bishop |
| 5,603,700 A | 2/1997 | Daneshvar |
| 5,603,711 A | 2/1997 | Parins |
| 5,611,803 A | 3/1997 | Heaven |
| 5,624,452 A | 4/1997 | Yates |
| 5,632,432 A | 5/1997 | Schulze |
| 5,637,110 A | 6/1997 | Pennybacker |
| 5,637,111 A | 6/1997 | Sutcu |
| 5,653,692 A | 8/1997 | Masterson |
| 5,658,281 A | 8/1997 | Heard |
| 5,662,662 A | 9/1997 | Bishop |
| 5,662,676 A | 9/1997 | Koninckx |
| 5,665,085 A | 9/1997 | Nardella |
| 5,665,100 A | 9/1997 | Yoon |
| 5,667,526 A | 9/1997 | Levin |
| 5,669,907 A | 9/1997 | Platt, Jr. |
| 5,673,840 A | 10/1997 | Schulze |
| 5,673,841 A | 10/1997 | Schulze |
| 5,674,184 A | 10/1997 | Hassler, Jr. |
| 5,674,220 A | 10/1997 | Fox |
| 5,675,184 A | 10/1997 | Matsubayashi |
| 5,680,982 A | 10/1997 | Schulze |
| 5,681,282 A | 10/1997 | Eggers |
| 5,683,385 A | 11/1997 | Kortenbach |
| 5,683,388 A | 11/1997 | Slater |
| 5,688,270 A | 11/1997 | Yates |
| 5,693,051 A | 12/1997 | Schulze |
| 5,697,949 A | 12/1997 | Giurtino |
| 5,700,261 A | 12/1997 | Brinkerhoff |
| 5,702,390 A | 12/1997 | Austin |
| 5,704,534 A | 1/1998 | Huitema |
| 5,707,369 A | 1/1998 | Vaitekunas |
| 5,709,680 A | 1/1998 | Yates |
| 5,711,472 A | 1/1998 | Bryan |

(56) References Cited

U.S. PATENT DOCUMENTS

| | | |
|---|---|---|
| 5,713,505 A | 2/1998 | Huitema |
| 5,713,896 A | 2/1998 | Nardella |
| 5,715,832 A | 2/1998 | Koblish |
| 5,718,703 A | 2/1998 | Chin |
| 5,720,719 A | 2/1998 | Edwards |
| 5,728,143 A | 3/1998 | Gough |
| 5,733,283 A | 3/1998 | Malis |
| 5,735,289 A | 4/1998 | Pfeffer |
| 5,735,848 A | 4/1998 | Yates |
| 5,735,849 A | 4/1998 | Baden |
| 5,741,285 A | 4/1998 | McBrayer |
| 5,743,906 A | 4/1998 | Parins |
| 5,746,750 A | 5/1998 | Prestel |
| 5,749,895 A | 5/1998 | Sawyer |
| 5,755,717 A | 5/1998 | Yates |
| 5,766,196 A | 6/1998 | Griffiths |
| 5,769,849 A | 6/1998 | Eggers |
| 5,776,130 A | 7/1998 | Buysse |
| 5,788,662 A | 8/1998 | Antanavich |
| 5,797,536 A | 8/1998 | Smith |
| 5,797,906 A | 8/1998 | Rhum |
| 5,797,941 A | 8/1998 | Schulze |
| 5,810,811 A | 9/1998 | Yates |
| 5,817,091 A | 10/1998 | Nardella |
| 5,817,092 A | 10/1998 | Behl |
| 5,823,066 A | 10/1998 | Huitema |
| 5,833,689 A | 11/1998 | Long |
| 5,833,690 A | 11/1998 | Yates |
| 5,836,990 A | 11/1998 | Li |
| 5,840,077 A | 11/1998 | Rowden |
| 5,855,576 A | 1/1999 | LeVeen |
| 5,860,975 A | 1/1999 | Goble |
| 5,891,142 A | 4/1999 | Eggers |
| 5,893,835 A | 4/1999 | Witt |
| 5,893,874 A | 4/1999 | Bourque |
| 5,931,835 A | 8/1999 | Mackey |
| 5,931,836 A | 8/1999 | Hatta |
| 5,954,720 A | 9/1999 | Wilson |
| 5,976,128 A | 11/1999 | Schilling |
| 5,979,453 A | 11/1999 | Savage |
| 6,003,517 A | 12/1999 | Sheffield |
| 6,004,319 A | 12/1999 | Goble |
| 6,007,561 A | 12/1999 | Bourque |
| 6,030,384 A | 2/2000 | Nezhat |
| 6,050,993 A | 4/2000 | Tu |
| 6,050,995 A | 4/2000 | Durgin |
| 6,056,744 A | 5/2000 | Edwards |
| 6,056,746 A | 5/2000 | Goble |
| 6,059,766 A | 5/2000 | Greff |
| 6,059,782 A | 5/2000 | Novak |
| 6,066,139 A | 5/2000 | Ryan |
| 6,068,626 A | 5/2000 | Harrington |
| 6,071,281 A | 6/2000 | Burnside |
| 6,074,386 A | 6/2000 | Gable |
| 6,077,287 A | 6/2000 | Taylor |
| 6,086,586 A | 7/2000 | Hooven |
| 6,090,106 A | 7/2000 | Goble |
| 6,093,186 A | 7/2000 | Gable |
| 6,096,037 A | 8/2000 | Mulier |
| 6,099,550 A | 8/2000 | Yoon |
| 6,123,701 A | 9/2000 | Nezhat |
| H1904 H | 10/2000 | Yates |
| 6,139,508 A | 10/2000 | Simpson |
| 6,142,992 A | 11/2000 | Cheng |
| 6,152,920 A | 11/2000 | Thompson |
| 6,152,932 A | 11/2000 | Ternstrom |
| 6,162,220 A | 12/2000 | Nezhat |
| 6,174,309 B1 | 1/2001 | Wrublewski |
| 6,179,832 B1 | 1/2001 | Jones |
| 6,203,541 B1 | 3/2001 | Keppel |
| 6,203,542 B1 | 3/2001 | Ellsberry |
| 6,206,877 B1 | 3/2001 | Kese |
| 6,210,406 B1 | 4/2001 | Webster |
| 6,212,426 B1 | 4/2001 | Swanson |
| 6,217,894 B1 | 4/2001 | Sawhney |
| 6,228,084 B1 | 5/2001 | Kirwan, Jr. |
| 6,234,178 B1 | 5/2001 | Goble |
| 6,241,139 B1 | 6/2001 | Milliman |
| 6,245,069 B1 | 6/2001 | Gminder |
| 6,254,601 B1 | 7/2001 | Burbank |
| 6,258,085 B1 | 7/2001 | Eggleston |
| 6,277,114 B1 | 8/2001 | Bullivant |
| 6,283,963 B1 | 9/2001 | Regula |
| 6,287,304 B1 | 9/2001 | Eggers |
| 6,290,715 B1 | 9/2001 | Sharkey |
| 6,293,942 B1 | 9/2001 | Goble |
| 6,293,946 B1 | 9/2001 | Thorne |
| 6,296,636 B1 | 10/2001 | Cheng |
| 6,306,134 B1 | 10/2001 | Goble |
| 6,312,430 B1 | 11/2001 | Wilson |
| 6,322,494 B1 | 11/2001 | Bullivant |
| 6,327,505 B1 | 12/2001 | Medhkour |
| 6,334,861 B1 | 1/2002 | Chandler |
| 6,350,274 B1 | 2/2002 | Li |
| 6,361,559 B1 | 3/2002 | Houser |
| 6,364,879 B1 | 4/2002 | Chen |
| 6,371,956 B1 | 4/2002 | Wilson |
| 6,391,024 B1 | 5/2002 | Sun |
| 6,391,029 B1 | 5/2002 | Hooven |
| 6,398,779 B1 | 6/2002 | Buysse |
| 6,398,781 B1 | 6/2002 | Goble |
| H2037 H | 7/2002 | Yates |
| 6,416,509 B1 | 7/2002 | Goble |
| 6,423,059 B1 | 7/2002 | Hanson |
| 6,428,550 B1 | 8/2002 | Vargas |
| 6,436,096 B1 | 8/2002 | Hareyama |
| 6,440,130 B1 | 8/2002 | Mulier |
| 6,443,952 B1 | 9/2002 | Mulier |
| 6,464,702 B2 | 10/2002 | Schulze |
| 6,485,486 B1 | 11/2002 | Trembly |
| 6,485,489 B2 | 11/2002 | Teirstein |
| 6,491,690 B1 | 12/2002 | Goble |
| 6,494,881 B1 | 12/2002 | Bales |
| 6,500,176 B1 | 12/2002 | Truckai |
| 6,514,252 B2 | 2/2003 | Nezhat |
| 6,517,530 B1 | 2/2003 | Kleven |
| 6,520,185 B1 | 2/2003 | Bommannan |
| 6,533,784 B2 | 3/2003 | Truckai |
| 6,546,933 B1 | 4/2003 | Yoon |
| 6,554,829 B2 | 4/2003 | Schulze |
| 6,564,806 B1 | 5/2003 | Fogarty |
| 6,565,560 B1 | 5/2003 | Goble |
| 6,565,561 B1 | 5/2003 | Goble |
| 6,584,360 B2 | 6/2003 | Francischelli |
| 6,610,060 B2 | 8/2003 | Mulier |
| 6,610,074 B2 | 8/2003 | Santilli |
| 6,613,048 B2 | 9/2003 | Mulier |
| 6,616,654 B2 | 9/2003 | Mollenauer |
| 6,616,659 B1 | 9/2003 | delaTorre |
| 6,619,529 B2 | 9/2003 | Green |
| 6,622,731 B2 | 9/2003 | Daniel |
| 6,623,482 B2 | 9/2003 | Pendekanti |
| 6,626,901 B1 | 9/2003 | Treat |
| 6,645,198 B1 | 11/2003 | Bommannan |
| 6,645,201 B1 | 11/2003 | Utley |
| 6,648,839 B2 | 11/2003 | Manna |
| 6,652,518 B2 | 11/2003 | Wellman |
| 6,656,177 B2 | 12/2003 | Truckai |
| 6,666,854 B1 | 12/2003 | Lange |
| 6,666,859 B1 | 12/2003 | Fleenor |
| 6,673,085 B1 | 1/2004 | Berg |
| 6,676,660 B2 | 1/2004 | Wampler |
| 6,682,526 B1 | 1/2004 | Jones |
| 6,682,527 B2 | 1/2004 | Strul |
| 6,695,840 B2 | 2/2004 | Schulze |
| 6,699,245 B2 | 3/2004 | Dinger |
| 6,719,754 B2 | 4/2004 | Underwood |
| 6,722,371 B1 | 4/2004 | Fogarty |
| 6,726,682 B2 | 4/2004 | Harrington |
| 6,736,814 B2 | 5/2004 | Manna |
| 6,743,229 B2 | 6/2004 | Buysse |
| 6,746,488 B1 | 6/2004 | Bales |
| 6,752,154 B2 | 6/2004 | Fogarty |
| 6,752,803 B2 | 6/2004 | Goldman |

(56) References Cited

U.S. PATENT DOCUMENTS

| | | |
|---|---|---|
| 6,755,827 B2 | 6/2004 | Mulier |
| 6,770,070 B1 | 8/2004 | Balbierz |
| 6,770,072 B1 | 8/2004 | Truckai |
| 6,773,435 B2 | 8/2004 | Schulze |
| 6,776,780 B2 | 8/2004 | Mulier |
| 6,808,525 B2 | 10/2004 | Latterell |
| 6,817,974 B2 | 11/2004 | Cooper |
| 6,821,273 B2 | 11/2004 | Mollenauer |
| 6,837,888 B2 | 1/2005 | Ciarrocca |
| 6,840,938 B1 | 1/2005 | Morley |
| 6,843,789 B2 | 1/2005 | Goble |
| 6,852,108 B2 | 2/2005 | Barry |
| 6,858,028 B2 | 2/2005 | Mulier |
| 6,877,647 B2 | 4/2005 | Green |
| 6,889,089 B2 | 5/2005 | Behl |
| 6,893,435 B2 | 5/2005 | Goble |
| 6,896,672 B1 | 5/2005 | Eggers |
| 6,896,673 B2 | 5/2005 | Hooven |
| 6,902,536 B2 | 6/2005 | Manna |
| 6,905,506 B2 | 6/2005 | Burbank |
| 6,908,463 B2 | 6/2005 | Treat |
| 6,913,579 B2 | 7/2005 | Truckai |
| 6,918,907 B2 | 7/2005 | Kelly |
| 6,918,909 B2 | 7/2005 | Ohyama |
| 6,923,803 B2 | 8/2005 | Goble |
| 6,923,806 B2 | 8/2005 | Hooven |
| 6,926,712 B2 | 8/2005 | Phan |
| 6,929,642 B2 | 8/2005 | Xiao |
| 6,936,048 B2 | 8/2005 | Hurst |
| 6,939,346 B2 | 9/2005 | Kannenberg |
| 6,953,461 B2 | 10/2005 | McClurken |
| 6,964,363 B2 | 11/2005 | Wales |
| 6,981,628 B2 | 1/2006 | Wales |
| 7,033,356 B2 | 4/2006 | Latterell |
| 7,055,731 B2 | 6/2006 | Shelton, IV |
| 7,063,699 B2 | 6/2006 | Hess |
| 7,090,637 B2 | 8/2006 | Danitz |
| 7,090,673 B2 | 8/2006 | Dycus |
| 7,090,685 B2 | 8/2006 | Kortenbach |
| 7,094,202 B2 | 8/2006 | Nobis |
| 7,094,235 B2 | 8/2006 | Francischelli |
| 7,101,371 B2 | 9/2006 | Dycus |
| 7,101,372 B2 | 9/2006 | Dycus |
| 7,101,373 B2 | 9/2006 | Dycus |
| 7,118,587 B2 | 10/2006 | Dycus |
| 7,125,409 B2 | 10/2006 | Truckai |
| 7,137,980 B2 | 11/2006 | Buysse |
| 7,159,750 B2 | 1/2007 | Racenet |
| 7,166,102 B2 | 1/2007 | Fleenor |
| 7,169,146 B2 | 1/2007 | Truckai |
| 7,179,254 B2 | 2/2007 | Pendekanti |
| 7,195,627 B2 | 3/2007 | Amoah |
| 7,208,005 B2 | 4/2007 | Frecker |
| 7,220,260 B2 | 5/2007 | Fleming |
| 7,238,195 B2 | 7/2007 | Viola |
| 7,250,048 B2 | 7/2007 | Francischelli |
| 7,255,697 B2 | 8/2007 | Dycus |
| 7,267,677 B2 | 9/2007 | Johnson |
| 7,270,664 B2 | 9/2007 | Johnson |
| 7,276,068 B2 | 10/2007 | Johnson |
| 7,278,991 B2 | 10/2007 | Morris |
| 7,291,143 B2 | 11/2007 | Swanson |
| 7,329,256 B2 | 2/2008 | Johnson |
| 7,364,577 B2 | 4/2008 | Wham |
| 7,367,972 B2 | 5/2008 | Francischelli |
| 7,410,483 B2 | 8/2008 | Danitz |
| 7,494,039 B2 | 2/2009 | Racenet |
| 7,506,790 B2 | 3/2009 | Shelton, IV |
| 7,513,898 B2 | 4/2009 | Johnson |
| 7,540,872 B2 | 6/2009 | Schechter |
| 7,543,730 B1 | 6/2009 | Marczyk |
| 7,549,564 B2 | 6/2009 | Boudreaux |
| 7,588,566 B2 | 9/2009 | Treat |
| 7,624,902 B2 | 12/2009 | Marczyk |
| 7,641,651 B2 | 1/2010 | Nezhat |
| 7,658,311 B2 | 2/2010 | Boudreaux |
| 7,703,653 B2 | 4/2010 | Shah |
| 7,794,461 B2 | 9/2010 | Eder |
| 7,803,156 B2 | 9/2010 | Eder |
| 7,862,565 B2 | 1/2011 | Eder |
| 7,942,874 B2 | 5/2011 | Eder |
| 2001/0029367 A1 | 10/2001 | Fleenor |
| 2002/0062123 A1 | 5/2002 | McClurken |
| 2002/0062136 A1 | 5/2002 | Hillstead |
| 2002/0107514 A1 | 8/2002 | Hooven |
| 2002/0124853 A1 | 9/2002 | Burbank |
| 2002/0128643 A1 | 9/2002 | Simpson |
| 2002/0151882 A1 | 10/2002 | Marko |
| 2002/0177848 A1 | 11/2002 | Truckai |
| 2002/0183738 A1 | 12/2002 | Chee |
| 2003/0018331 A1 | 1/2003 | Dycus |
| 2003/0078577 A1 | 4/2003 | Truckai |
| 2003/0144652 A1 | 7/2003 | Baker |
| 2003/0144653 A1 | 7/2003 | Francischelli |
| 2003/0158547 A1 | 8/2003 | Phan |
| 2003/0171745 A1 | 9/2003 | Francischelli |
| 2003/0199869 A1 | 10/2003 | Johnson |
| 2003/0216726 A1 | 11/2003 | Eggers |
| 2003/0229344 A1 | 12/2003 | Dycus |
| 2003/0236549 A1 | 12/2003 | Bonadio |
| 2004/0006339 A1 | 1/2004 | Underwood |
| 2004/0010245 A1 | 1/2004 | Cerier |
| 2004/0049185 A1 | 3/2004 | Latterell |
| 2004/0068274 A1 | 4/2004 | Hooven |
| 2004/0097919 A1 | 5/2004 | Wellman |
| 2004/0122423 A1 | 6/2004 | Dycus |
| 2004/0143263 A1 | 7/2004 | Schechter |
| 2004/0199226 A1 | 10/2004 | Shadduck |
| 2004/0236316 A1 | 11/2004 | Danitz |
| 2004/0236320 A1 | 11/2004 | Protsenko |
| 2004/0236326 A1 | 11/2004 | Schulze |
| 2005/0010212 A1 | 1/2005 | McClurken |
| 2005/0015085 A1 | 1/2005 | McClurken |
| 2005/0021024 A1 | 1/2005 | Hooven |
| 2005/0021026 A1 | 1/2005 | Bally |
| 2005/0021027 A1 | 1/2005 | Shields |
| 2005/0033276 A1 | 2/2005 | Adachi |
| 2005/0033277 A1 | 2/2005 | Clague |
| 2005/0033278 A1 | 2/2005 | McClurken |
| 2005/0033282 A1 | 2/2005 | Hooven |
| 2005/0070895 A1 | 3/2005 | Ryan |
| 2005/0070978 A1 | 3/2005 | Bek |
| 2005/0090819 A1 | 4/2005 | Goble |
| 2005/0096645 A1 | 5/2005 | Wellman |
| 2005/0096694 A1 | 5/2005 | Lee |
| 2005/0107781 A1 | 5/2005 | Ostrovsky |
| 2005/0107784 A1 | 5/2005 | Moses |
| 2005/0113817 A1 | 5/2005 | Isaacson |
| 2005/0113820 A1 | 5/2005 | Goble |
| 2005/0113826 A1 | 5/2005 | Johnson |
| 2005/0119654 A1 | 6/2005 | Swanson |
| 2005/0131390 A1 | 6/2005 | Heinrich |
| 2005/0137591 A1 | 6/2005 | Barry |
| 2005/0149073 A1 | 7/2005 | Arani |
| 2005/0171530 A1 | 8/2005 | Hooven |
| 2005/0171533 A1 | 8/2005 | Latterell |
| 2005/0187561 A1 | 8/2005 | Lee-Sepsick |
| 2005/0192568 A1 | 9/2005 | Truckai |
| 2005/0192633 A1 | 9/2005 | Montpetit |
| 2005/0196421 A1 | 9/2005 | Hunter |
| 2005/0203500 A1 | 9/2005 | Saadat |
| 2005/0203504 A1 | 9/2005 | Wham |
| 2005/0209664 A1 | 9/2005 | Hunter |
| 2005/0226682 A1 | 10/2005 | Chersky |
| 2005/0256522 A1 | 11/2005 | Francischelli |
| 2005/0256524 A1 | 11/2005 | Long |
| 2005/0261676 A1 | 11/2005 | Hall |
| 2006/0011699 A1 | 1/2006 | Olson |
| 2006/0025765 A1 | 2/2006 | Landman |
| 2006/0025812 A1 | 2/2006 | Shelton |
| 2006/0041254 A1 | 2/2006 | Francischelli |
| 2006/0052778 A1 | 3/2006 | Chapman |
| 2006/0052779 A1 | 3/2006 | Hammill |
| 2006/0064084 A1 | 3/2006 | Haemmerich |

(56) References Cited

U.S. PATENT DOCUMENTS

| | | |
|---|---|---|
| 2006/0064085 A1 | 3/2006 | Schechter |
| 2006/0079872 A1 | 4/2006 | Eggleston |
| 2006/0142751 A1 | 6/2006 | Treat |
| 2006/0167451 A1 | 7/2006 | Cropper |
| 2006/0189980 A1 | 8/2006 | Johnson |
| 2006/0190029 A1 | 8/2006 | Wales |
| 2006/0190031 A1 | 8/2006 | Wales |
| 2006/0199999 A1 | 9/2006 | Ikeda |
| 2006/0217709 A1 | 9/2006 | Couture et al. |
| 2006/0226196 A1 | 10/2006 | Hueil |
| 2006/0229665 A1 | 10/2006 | Wales |
| 2006/0253117 A1 | 11/2006 | Hovda |
| 2006/0258954 A1 | 11/2006 | Timberlake |
| 2006/0259034 A1 | 11/2006 | Eder |
| 2006/0259035 A1 | 11/2006 | Nezhat |
| 2006/0271037 A1 | 11/2006 | Maroney |
| 2006/0271038 A1 | 11/2006 | Johnson |
| 2006/0271042 A1 | 11/2006 | Latterell |
| 2006/0287674 A1 | 12/2006 | Ginn |
| 2006/0289602 A1 | 12/2006 | Wales |
| 2006/0293655 A1 | 12/2006 | Sartor |
| 2007/0005061 A1 | 1/2007 | Eder |
| 2007/0055231 A1 | 3/2007 | Dycus |
| 2007/0062017 A1 | 3/2007 | Dycus |
| 2007/0073340 A1 | 3/2007 | Shelton |
| 2007/0128174 A1 | 6/2007 | Kleinsek |
| 2007/0129726 A1 | 6/2007 | Eder |
| 2007/0173804 A1 | 7/2007 | Wham |
| 2007/0173805 A1 | 7/2007 | Weinberg |
| 2007/0173811 A1 | 7/2007 | Couture |
| 2007/0179340 A1 | 8/2007 | Jorgensen |
| 2007/0179497 A1 | 8/2007 | Eggers |
| 2007/0185482 A1 | 8/2007 | Eder |
| 2007/0185518 A1 | 8/2007 | Hassier |
| 2007/0208330 A1 | 9/2007 | Treat |
| 2007/0244538 A1 | 10/2007 | Eder |
| 2007/0250113 A1 | 10/2007 | Hegeman |
| 2007/0260242 A1 | 11/2007 | Dycus |
| 2007/0265613 A1 | 11/2007 | Edelstein |
| 2007/0282318 A1 | 12/2007 | Spooner |
| 2007/0282320 A1 | 12/2007 | Buysse |
| 2007/0299439 A1 | 12/2007 | Latterell |
| 2008/0039835 A1 | 2/2008 | Johnson |
| 2008/0045947 A1 | 2/2008 | Johnson |
| 2008/0114356 A1 | 5/2008 | Johnson |
| 2008/0172052 A1 | 7/2008 | Eder |
| 2008/0188844 A1 | 8/2008 | McGreevy |
| 2008/0188868 A1 | 8/2008 | Weitzner |
| 2008/0195093 A1 | 8/2008 | Couture |
| 2008/0221565 A1 | 9/2008 | Eder |
| 2008/0228179 A1 | 9/2008 | Eder |
| 2008/0262538 A1 | 10/2008 | Danitz |
| 2008/0275446 A1 | 11/2008 | Messerly |
| 2008/0308607 A1 | 12/2008 | Timm |
| 2009/0018535 A1 | 1/2009 | Schechter |
| 2009/0112230 A1 | 4/2009 | Jinno |
| 2009/0138006 A1 | 5/2009 | Bales |
| 2009/0149853 A1 | 6/2009 | Shields |
| 2009/0157071 A1 | 6/2009 | Wham |
| 2009/0157072 A1 | 6/2009 | Wham |
| 2009/0157075 A1 | 6/2009 | Wham |
| 2009/0171354 A1 | 7/2009 | Deville |
| 2009/0182323 A1 | 7/2009 | Eder |
| 2009/0198272 A1 | 8/2009 | Kerver |
| 2009/0209953 A1 | 8/2009 | Schoenman |
| 2009/0234347 A1 | 9/2009 | Treat |
| 2009/0240245 A1 | 9/2009 | Deville |
| 2009/0299367 A1 | 12/2009 | Ginnebaugh |
| 2010/0042093 A9 | 2/2010 | Wham |
| 2010/0076427 A1 | 3/2010 | Heard |
| 2010/0094282 A1 | 4/2010 | Kabaya |
| 2010/0280508 A1 | 11/2010 | Eder |
| 2010/0298823 A1 | 11/2010 | Cao |
| 2011/0009863 A1 | 1/2011 | Marczyk |
| 2011/0106078 A1 | 5/2011 | Mueller |
| 2011/0184404 A1 | 7/2011 | Walberg |
| 2011/0202058 A1 | 8/2011 | Eder |
| 2011/0230875 A1 | 9/2011 | Walberg |
| 2012/0130367 A1 | 5/2012 | Garrison |
| 2012/0215220 A1 | 8/2012 | Manzo |

FOREIGN PATENT DOCUMENTS

| | | |
|---|---|---|
| CN | 1826083 | 8/2006 |
| CN | 102596080 | 7/2012 |
| EP | 487269 | 5/1991 |
| EP | 440385 | 7/1991 |
| EP | 502268 | 9/1992 |
| EP | 562195 | 9/1993 |
| EP | 658333 | 6/1995 |
| EP | 536998 | 4/1996 |
| EP | 518230 | 5/1996 |
| EP | 0737446 | 10/1996 |
| EP | 875209 | 4/1998 |
| EP | 878169 | 11/1998 |
| EP | 640315 | 12/1998 |
| EP | 923907 | 6/1999 |
| EP | 640317 | 9/1999 |
| EP | 771176 | 7/2000 |
| EP | 1050278 | 11/2000 |
| EP | 1064886 | 1/2001 |
| EP | 833593 | 2/2001 |
| EP | 1254637 | 11/2002 |
| EP | 0717960 | 2/2003 |
| EP | 1293169 | 3/2003 |
| EP | 1293170 | 3/2003 |
| EP | 869742 | 5/2003 |
| EP | 1330989 | 7/2003 |
| EP | 1330991 | 7/2003 |
| EP | 1344498 | 9/2003 |
| EP | 873089 | 10/2003 |
| EP | 742696 | 11/2003 |
| EP | 1041933 | 3/2004 |
| EP | 959784 | 4/2004 |
| EP | 0794735 | 7/2004 |
| EP | 1004277 | 7/2004 |
| EP | 959786 | 9/2004 |
| EP | 913126 | 10/2004 |
| EP | 956827 | 10/2004 |
| EP | 1472984 | 11/2004 |
| EP | 1025807 | 12/2004 |
| EP | 1486177 | 12/2004 |
| EP | 1518498 | 3/2005 |
| EP | 1518499 | 3/2005 |
| EP | 927543 | 4/2005 |
| EP | 1532933 | 5/2005 |
| EP | 1621146 | 2/2006 |
| EP | 1632192 | 3/2006 |
| EP | 1637086 | 3/2006 |
| EP | 1645237 | 4/2006 |
| EP | 1747761 | 1/2007 |
| EP | 1767164 | 3/2007 |
| EP | 1852081 | 11/2007 |
| EP | 1862138 | 12/2007 |
| EP | 1039862 | 5/2008 |
| EP | 1707143 | 6/2008 |
| EP | 1958583 | 8/2008 |
| EP | 2065006 | 6/2009 |
| EP | 2106764 | 10/2009 |
| EP | 2110093 | 10/2009 |
| JP | 11070123 | 3/1999 |
| JP | 11070124 | 3/1999 |
| JP | 2003061969 A | 3/2003 |
| JP | 2003088534 | 3/2003 |
| JP | 2004049566 | 2/2004 |
| JP | 2005021703 | 1/2005 |
| JP | 2005144193 | 6/2005 |
| JP | 2006223872 | 8/2006 |
| JP | 2007502198 | 2/2007 |
| JP | 2009107087 A | 5/2009 |
| JP | 2011510800 A | 4/2011 |
| WO | 9116856 | 11/1991 |
| WO | 9222257 | 12/1992 |
| WO | 9308754 | 5/1993 |

(56) References Cited

FOREIGN PATENT DOCUMENTS

| | | |
|---|---|---|
| WO | 9400060 | 1/1994 |
| WO | 9426179 | 11/1994 |
| WO | 9502371 | 1/1995 |
| WO | 9514436 | 6/1995 |
| WO | 9525471 | 9/1995 |
| WO | 9605776 | 2/1996 |
| WO | 1996016605 | 6/1996 |
| WO | 9623449 | 8/1996 |
| WO | 9724073 | 7/1997 |
| WO | 9724074 | 7/1997 |
| WO | 9724995 | 7/1997 |
| WO | 9812999 | 4/1998 |
| WO | 9843548 | 10/1998 |
| WO | 9853750 | 12/1998 |
| WO | 9923933 | 5/1999 |
| WO | 9951155 | 10/1999 |
| WO | 9951158 | 10/1999 |
| WO | 9952459 | 10/1999 |
| WO | 9956646 | 11/1999 |
| WO | 0013192 | 3/2000 |
| WO | 0013193 | 3/2000 |
| WO | 0047124 | 8/2000 |
| WO | 0112090 | 2/2001 |
| WO | 0135846 | 5/2001 |
| WO | 0154602 | 8/2001 |
| WO | 0158372 | 8/2001 |
| WO | 0158373 | 8/2001 |
| WO | 0182812 | 11/2001 |
| WO | 0224092 | 3/2002 |
| WO | 0236028 | 5/2002 |
| WO | 0267798 | 7/2002 |
| WO | 0258542 | 8/2002 |
| WO | 02071926 | 9/2002 |
| WO | 02080783 | 10/2002 |
| WO | 03001986 | 1/2003 |
| WO | 03024348 | 3/2003 |
| WO | 03088806 | 10/2003 |
| WO | 0396886 | 11/2003 |
| WO | 03103522 | 12/2003 |
| WO | 2004032596 | 4/2004 |
| WO | 2004032776 | 4/2004 |
| WO | 2004073490 | 9/2004 |
| WO | 2004098383 | 11/2004 |
| WO | 04103156 | 12/2004 |
| WO | 2004105578 | 12/2004 |
| WO | 2005009213 | 2/2005 |
| WO | 2005034729 | 4/2005 |
| WO | 2005079901 | 9/2005 |
| WO | 05115251 | 12/2005 |
| WO | 2006026520 | 3/2006 |
| WO | 2006060431 | 6/2006 |
| WO | 06124601 | 11/2006 |
| WO | 2006124518 | 11/2006 |
| WO | 2007002227 | 1/2007 |
| WO | 2007082061 | 7/2007 |
| WO | 2007146842 | 12/2007 |
| WO | 2008094554 | 8/2008 |
| WO | 2008094564 | 8/2008 |
| WO | 2008124112 | 10/2008 |
| WO | 2009070780 | 6/2009 |
| WO | 2009100366 A2 | 8/2009 |
| WO | 2009154976 | 12/2009 |
| WO | 2010104755 | 9/2010 |
| WO | 2011097469 | 8/2011 |

OTHER PUBLICATIONS

European Office Action dated Aug. 22, 2016 for European Application No. 15183442.1, 5 pages.
European Office Action dated Aug. 22, 2016 for European Application No. 15183443.9, 4 pages.
Extended European Search Report dated Jan. 5, 2016 for European Application No. 15183441.3.
Korean Office Action issued in Korean Application No. 10-2010-7017567 dated May 7, 2015 (Translation Only).
Office Action dated Jul. 13, 2015 in U.S. Appl. No. 12/027,231.
Extended European Search Report dated Dec. 15, 2015 for European Application No. 15183443.9.
Extended European Search Report dated Dec. 15, 2015 for European Application No. 15183442.1.
Abu-Rustum, NR, et al., "Transperitoneal Laparoscopic Pelvic and Para-Aortic Lymph Node Dissection Using Argon-Beam Coagulator and Monopolar Instruments: An 8-Year Study and Description of Technique,"Jun. 2003; Gynecol Oncol. 89(3): 504-13; Memorial Sloan-Kettering Cancer Center, 1275 York Avenue, New York, NY 10021, USA gynbreast@mskcc.org.
Aoki et al.; Thoracoscopic resection of the lung with the ultrasonic scalpel; Ann thorac Surg; vol. 67; No. 4; pp. 1181-1183; Apr. 1999.
Arthrocare receives clearance to market coblation-based devices for gynecology and laparoscopic surgery: clearance includes plasma forceps and 21 specific indications; Business Wire; p. 524; Oct. 25, 2001.
Australian Patent Examination Report No. 1 dated Mar. 13, 2013 for Patent Application No. 2009212240.
Bergamaschi et al.; Laparoscopic intracorporeal bowel resection with ultrasound versus electrosurgical dissection; JSLS; vol. 5; No. 1; pp. 17-20; Jan.-Mar. 2001.
Briani, S. et al.; Pseudo-Bipolar Electrocoagulation With a Branched Forceps; 1967; Minerva Neurochir.; 11 (3): 306-11.
Cakan. A. et al.: The Histological Effect of Harmonic Scalpel and Electrocautery In Lung Resections. An Experimental Study In a Rat Model: Feb. 2004; J Cardiovasc Surq (Torino).; 45 (1): 63-5; Department of Thoracic Surgery, Ege University School of Medicine, Izmir, Turkey, alpcakan@gohip.com.
Canadian Patent Examination Report No. May 23, 2013 for Patent Application No. 2,713,983.
Ceviker. N. et al.; A New Coated Bipolar Coagulator: Technical Note; 1998; Acta Neurochir (Wien).; 140 (6): 619-20; Department of Neurosurgery, Faculty of Medicine, Gazi University, Ankara, Turkey.
Cherchi. PL. et al.: Utility of Bipolar Electrocautery Scissors for Cervical Conization: 2002; Eur J Gynaecol Oncol. 2002; 23 (2): 154-6; Department of Pharmacology, Gynecology and Obstetrics, University of Sassari, Italy.
Chinese Application Serial No. 200980104230.X, Office Action dated Nov. 19, 2012 (with English language translation).
Circon Corporation—Company Report; Investext, p. 1-13; Jan. 3, 1995.
Colvin. D.P. et al.: Development of an Endoscopic RF Hyperthermia System for Deep Tumor Therapy: 1987: American Society of Mechanical Engineers. Heat Transfer Division, (Publication) HTD v. 95. Publ by ASME (BED-v 7), New York, NY, USA p. 25-30.
Corson. S.L.: Two New Laparoscopic Instruments: Bipolar Sterilizing Forceps and Uterine Manipulator: Jan.-Feb. 1977; Medical Instrumentation vol. 11, No. 1 p. 7-8;; USA.
Curon Announces The Publication of Data Supporting Durabilityy and Effectiveness of Stretta (R) System:—Positive One Year Follow-Up Data of U.S. Clinical Trial Published in Gastrointestinal Endoscopy: Feb. 7, 2002; PR Newswire, pNYTH 10307022002.
Curon Medical Announces Presentation of Positive Clinical Study Results of Stretta(R) Procedure for Gastroesophageal Reflux Disease (GERD): Mar. 20, 2002; PR Newswire,PNYW07920032002.
Daniel. P. et al.: Ultrasonic Sealing of the Lung Parenchyma After Atypical Resection: ZEXP Chir Transplant Kunstliche Organe. 1987: 20 (2): 117-21.
Digeronimo. EM et al.: Cut-Blot-Coagulate: A New Time Saving Device: Nov. 1982 Plast Reconstr Surg.; 70 (5): 639-40.
Dubuc-Lissoir. J.: Use of a New Energy-Based Vessel Ligation Device During Laparoscopic Gynecologic Oncologic Surgery: Mar. 2003 Surg Endosc.: 17 (3): 466-8.Epub Oct. 31, 2002; Department of Obstetrics and Gynecology, CHUM—Notre-Dame Hospital, Pavilion Charles-Simard, 2065 Alexandre-de-Seve, 4th Floor, Montreal, Quebec, Canada, H2L 2W5. josee.dubuc-lissoir.chum@ssss.gouv.qc.ca.

(56) References Cited

OTHER PUBLICATIONS

Eder, Joseph C.; U.S. Appl. No. 12/200,798 entitled "Assisted systems and methods for performing transvaginal hysterectomies," filed Aug. 28, 2008.

Eichfeld et al.; Evaluation of ultracision in lung metastatic surgery; Ann Thorac Surg; vol. 70; No. 4; pp. 1181-1184; Oct. 2000.

Enable Medical Introduces Second Generation Bipolar Scissors: Dec. 1998: Health Industry Today, pNA.

Entire patent prosecution history of U.S. Appl. No. 12/027,231, filed Feb. 6, 2008, entitled, "Method and Apparatus for Articulating the Wrist of a Laparoscopic Grasping Instrument.".

Entire patent prosecution history of U.S. Appl. No. 13/070,391, filed Mar. 23, 2011, entitled, "Articulable Electrosurgical Instrument With a Stabilizable Articulation Actuator," now U.S. Pat. No. 8,870,867, issued Oct. 28, 2014.

ERBE Elektromedizin GmbH; ERBE BiClamp Brochure; downloaded Jan. 24, 2011; 6 pgs., © 2011, http://www.erbe-med.corn/erbe/media/Marketingmaterialien/85100-139_ERBE_EN_BiClamp_D024676.pdf.

Ercoli. A. et al.: Radiofrequency Bipolar Coagulation for Radical Hysterectomy: Technique. Feasibility and Complications: Mar.-Apr. 2003 Int J Gynecol Cancer.: 13 (2):187-91 department of Obstetrics and Gynecology, Catholic University, Rome, Italy.

European Application Serial No. 09707446.2, Supplementary European Search Report mailed Oct. 9, 2012.

Everest Medical Announces Introduction of 3mm Bipolar Forceps: Oct. 2, 1996: PRNewswire, p1002MNW021.

Everest Medical Discusses Patent Status: Forecasts $1 Million Revenue First Quarter: Introduces Next Generation Bipolar Scissors: Mar. 31, 1994; PR Newswire, pN/A.

Everest Medical Introduces New Quadripolar (TM) Cutting Forceps at the Global Congress of Gynecologic Endoscopy Meeting: Nov. 8, 1999; PR Newswire p. 8927.

Everest Medical Releases Bicoag (TM) for Use in Treating Bleeding Ulcers: May 9, 1990:News Release, p. 1.

Everest Medical Reports Record First Quarter Results: Introduces Next Generation Bipolar Scissors: Apr. 19, 1994; PR Newswire, pN/A.

First Office Action for Chinese Application No. CN 200980104230 dated Jan. 18, 2012 (w/ English language translation).

Forestier D. et al.: Do Bipolar Scissors Increase Postoperative Adhesions? An Experimental Double-Blind Randomized Trial: Nov. 2002, Ann Chir.; 127 (9): 680-4; Service de chirurgie generale et digestive, Hotel-Dieu, boulevard Leon-Malfreyt, 63058 Clermont-Ferrand, France.

Gerasin VA et al.: Endoscopic Electrosurgery of the Trachea and Bronchi; Sep.- Oct. 1988 Grudn Khir; (5): 50-3.

Gyr. T. et al.: Minimal Invasive Laparoscopic Hysterectomy With Ultrasonic Scalpel: Jun. 2001 Am J Surg.; 181 (6): 516-9; Department of Obstetrics and Gynecology, Regional Hospital, Lugano, Switzerland.

Gyrus ACMI (An Olympus Company); PKS Seal (product page);http://www.gyrusacmi.com/user/display.cfm?display=product&pid=9024; downloaded Jan. 24, 2011; 1 page.

Gyrus Medical: Cutting Forceps Forceps:http://www.gyrusgroup.com/medical/products_item.asp?id=7, downloaded 2005.

Gyrus Medical: LP Scissors:http://www.gyrusgroup.com/medical/productsitem.asp?id=11, downloaded 2005.

Gyrus Medical: Lyons TM Dissecting Forceps: http://www.gyrusgroup.com/medical/products item.asp?id=8, downloaded 2005.

Gyrus Medical: Micro/Macro-Jaw Forceps: http://www.gyrusgroup.com/medical/products item.asp?id=13, downloaded 2005.

Gyrus Medical: Seal TM Open Forceps; http://www.gyrusgroup.com/medical/products item.asp?id=15, downloaded 2005.

Gyrus Medical; Seal Open Forceps (Product Information); downloaded Oct. 20, 2005.

Harrell. AG et al.: Energy Sources in Laparoscopy: Sep. 2004 Semin Laparosc Surg.; 11 (3): 201-9; Carolinas Laparoscopic and Advanced Surgery Program, Carolinas Medical Center, Charlotte, NC 28203, USA.

Hayashi et al.; Experimental and clinical evaluation of the harmonic scalpel in thoracic surgery; Kurume Med J; vol. 46; No. 1; pp. 25-29; 1999.

Hefni et al.; Safety and efficacy of using the ligasure vessel sealing system for securing the pedicles in vaginal hysterectomy: randomized controlled trial; BJOG; vol. 112; No. 3; pp. 329-333; Mar. 2005.

Heniford BT et al.: Initial Results With an Electrothermal Bipolar Vessel Sealer: Aug. 2001 Surg Endosc.; 15 (8); 799-801. Epub May 14, 2001; Carolinas Laparoscopic and Advanced Surgery Program, Department of General Surgery, Carolinas Medical Center, 1000 Blythe Boulevard, MEB #601, Charlotte, NC. USA.

International Preliminary Report on Patentability for International Application No. PCT/IB2013/002133 dated Mar. 31, 2015.

International Search Report and Written Opinion of International Application No. PCT/IB2013/02133 dated Feb. 19, 2014.

Japanese Patent Examination Report No. dated Apr. 16, 2013 for Patent Application No. 2010-546064 (with English language translation).

Kamat. AA et al.: Superiority of Electrocautery Over the Suture Method for Achieving Cervical Cone Bed Hemostasis: Oct. 2003 Obstet Gynecol.: 102 (4): 726-30; Department of Obstetrics and Gynecology, Baylor College of Medicine, Houston, Texas 77030, USA. akamat@bcm.tmc.edu.

Kato. K. et al.: A Computer Based. Temperature Controlled Bipolar Electrocoagulation System: Sep. 1996 Eur J Obstet Gynecol Reprod Biol.; 68 (1-2): 119-22; Department of Obstetrics and Gynecology, University of Essen, Germany.

Kennedy. JS et al.: High-Burst-Strength. Feedback-Controlled Bipolar Vessel Sealing; Jun. 1998 Surg Endosc.; 12 (6): 876-8; Valleylab, Inc., 5920 Longbow Drive, Boulder, CO 80301, USA.

Kim et al.; Design and fabrication of a locomotive mechanism for capsule-type endoscopes using shape memory alloys (SMAs); IEEE/ASME Trans on Mechatronics; vol. 10; No. 1; pp. 77-86; Feb. 2005.

Koch. C. et al.: Determination of Temperature Elevation in Tissue During the Application of the Harmonic Scalpel; Feb. 2003 Ultrasound Med Biol.: 29 (2): 301-9: Ultrasonics Section, Physikalisch-Technische Bundesanstalt Braunschweig, B raunschweig, Germany. christian.koch@ptb.de.

Kohler C. et al.: Laparoscopic Coagulation of the Uterine Blood Supply in Laparoscopic-Assisted Vaginal Hysterectomy Is Associated With Less Blood Loss: 2004Eur J Gynaecol Oncol.; 25 (4): 453-6; Department of Gynecology, Friedrich Schiller University, Jena, Germany.

Koss et al.; U.S. Appl. No. 12/748,229 entitled "Impedance mediated power delivery for electrosurgery," filed Mar. 26, 2010.

Koss et al.; U.S. Appl. No. 12/907,646 entitled "Impedance mediated control of power delivery for electrosurgery," filed Oct. 19, 2010.

Kovac; Transvaginal hysterectomy; rationale and surgical approach; Obstet. Gynecol.; vol. 103; pp. 1321-1325; 2004.

Kung, RC et al: A New Bipolar System for Performing Operative Hysetroscopy in Normal Saline; Aug. 1998; 6 (3): 331-6J Am Assoc Gynecol Laparosc.http://www.ncbi.nlm.nih.gov/entrez/query.fcgi?cmd=Retrieve&db=pubmed&dopt=Abstract& list uids=10459037&query hl=1.

Kwok. A. et al.: Comparison of Tissue Injury Between Laparosonic Coagulating Shears and Electrosurgical Scissors in the Sheep Model: Aug. 2001 J Am Assoc Gynecol Laparosc.; 8 (3): 378-84; Department of Endosurgery, Women's Institute, University of Sydney, Australia.

Landman J. et al.: Evaluation of a Vessel Sealing System. Bipolar Electrosurgery. Harmonic Scalpel. Titanium Clips. Endoscopic Gastrointestinal Anastomosis Vascular Staples and Sutures for Arter lal and Venous Ligation in a Porcine Model: Feb. 2003 J Urol.; 169 (2): 697-700; Department of Surgery (Division of Urology), Washington University School of Medicine, St. Louis, Missouri, USA.

(56) References Cited

OTHER PUBLICATIONS

Lantis. JC II et al.: Comparison of Coagulation Modalities in Surgery: Dec. 1998 J Laparoendosc Adv Surg Tech A.; 8 (6): 381-94; Surgical Research Laboratory, New England Medical Center, Boston, Massachusetts, USA.
Laparoscopic Lasers Vs. Electrosurgery: Debated Technology Choices: Jun. 6. 1991: The BBI Newsletter, v. 14, n. 6, pN/A.
Levy. Barbara: Use of a New Vessel Ligation Device During Vaginal Hysterectomy: As presented at FIGO 2000, Washington, D.C.; University of Washington School of Medicine; Federal Way, Washington, USA; © 2000 Valleylab.
Levy. Barbara et al.: Update on Hysterectomy: New Technologies and Techniques; Feb. 2003; http://www.obgmanagement.com/supplements/pdf/hysterectomy.pdf; A supplement to OBG Management.
Lin et al.; Application of ultrasonic scalpel in gynecologic operative laparoscopy; Chin Med J (Engl.); vol. 114; no. 12; pp. 1283-1285; Dec. 2001.
Live Tissue Connect Technologies; company profile;(http://www.onemedplace.com/database/compdisplay print.php?CompanyID=11508); 1 pg.; Oct. 19, 2010 (downloaded Feb. 7, 2011).
Lyons et al.; an innovative bipolar instrument for laparoscopic surgery; Jsls; vol. 9; no. 1; pp. 39-41; Jan-Mar 2005.
Market and Technology Updates: Bipolar Endoscopic Device: Jan. 24. 1990: the Bbi Newsletter, v. 13, n. 1, pN/a; T3.
Matsumura Y. et al.: New Surgical Technique of Pulmonary Segmentectomy by Ultrasonic Scalpel and Absorbable Sealing Materials: 2004 Jan. Kyobu Geka.: 57 (1): 31-'7; Department of Thoracic Surgery, Institute of Development, Aging and Cancer, Tohoku University, Sendai, Japan T3.
McCLURKEN et al.; Collagen shrinkage and vessel sealing; Technical brief #300. Dover, Nh: Tissue Link Medical; 2001.
Mundt. C. et al.: Advanced Sensor Systems for Improved Labor and Fetal Monitoring: 1998; Isa Tech/Expo Technology Update Conference Proceedings v. 2 n. 2, p. 79-89; 1998 T3.
Nezhat et al.; U.S. Pat. App. # 08/948,282 entitled "Method and systems for organ resection," filed Oct. 9, 1997.
Nikolov, N. et al.; Remote Controllable Vessel Occlusion Device: 1978 Jan. Med Biol Eng Comput.; 16 (1): 116-7 T3.
Nojarov et al.; High-energy scissors mode; Rhys Rev C Nucl Rhys; vol. 51; no. 5; pp. 2449-2456; 1995 (http://arxiv.org/abs/nucl-th/9502001v1).
Notice of Allowance issued in Application No. 13/070,391, dated Jul. 2, 2014.
Office Action for Appln. No. 13/070,391, filed Mar. 23, 2011, dated Mar. 7, 2014.
Office Action from the Mexican Institute of the Industrial Property issued in Mexican Patent Application No. Mx/a/2010/008634 on Jun. 11, 2013.
Ou. Cs et al.: Total Laparoscopic Hysterectomy Using Multifunction Grasping. Coagulating, and Cutting Forceps: 2004 Apr, J Laparoendosc Adv Surg Tech a.; 14 (2): 67-71; Department of Research and Development, Northwest Hospital and University of Washington School of Medicine, Seattle, Washington 98155, Usa. cou@nwhsea.org T3.
Parikh et al.; Three dimensional virtual reality model of the normal female pelvic floor; Annals of Bimedical Engineering; vol. 32; pp. 292-296; Feb. 2004.
Pavlov. IUV et al.: Ultrasonic Technologies In Diagnosis and Treatment of Patients With Surgical Diseases of Lungs and Pleura; 2003 Khirurgiia (Mosk).; (8): 30-4.
Petrakis. IE et al.: Use of the Ligasure Vessel Sealer in Total Abdominal Hysterectomy: Jun. 2005 Int J Gynaecol Obstet.; 89 (3): 303-4. Epub Mar. 2, 2005; Department of General Surgery, University General Hospital of Heraklion, University of Crete, Heraklion, Crete, Greece, petrakis@post.com.
Quadripolar Cutting Forceps Introduced by Everest Medical: Jan. 2000; Health Industry Today, v. 63, n. 1, pNA.

Radiofrequency energy proven effective against leading cause of obstructive sleep apnea; Business Wire; , Sep. 14, 1998, 4 pgs.
Raestrup. H. et al.: Dissection Technique Is Ultrasound the Best Method?: 2001 Kongressbd Dtsch Ges Chir Kohgr.; 118; 69-70; Universitatsklinik Fur Allgemeine Chirurgie, Hoppe-Seyler-Strasse 3, 72076 Tubingen.
Refractec, Inc.; Medical Use of Radiofrequency (RF) Energy; (http://www.locateadoc.com/Site_Tools/Print.cfm); 2 pgs; Aug. 23, 2008.
Robinson JL et al.: Bipolar Diathermy: Sep. 1974 Can J Surg., 17 (5): 287-91.
Sages 2001 Hands-On Course I—Taking it to the Next Level: Advanced Laparoscopic Techniques; http://www.sages.org/01/program/syllabi/ho1.html#schirme; 24 pgs; downloaded Oct. 5, 2005.
Sages 2001 Nurses Program, Session 1;http://sages.org/01program/syllabi/nurse/nurse.html; downloaded Jan. 24, 2011; 5 pgs.
Srisombut. C. et al.: Laparoscopic Hysterectomy Using Laparosonic Coagulating Shears: Experience of 15 Cases: Aug. 2000 J Med Assoc Thai.; 83 (8): 915-20; Department of Obstetrics and Gynecology, Faculty of Medicine, Ramathibodi Hospital, Mahidol University, Bangkok, Thailand.
Stanojevic. D. et al.: An Ultrasonic Scalpel for Laparoscopic Gynecologic Surgery: May-Jun. 1998 Srp Arh Celok Lek.; 126 (5-6): 214-6; Narodni Front Department of Gynecology and Obstetrics, Dr. Dragisha Mishovitsh Medical Centre, Belgrade.
Sugi. K. et al.: Use of the Bipolar Vessel Sealing System in Lung Resection: Jul. 2003 Kyobu Geka.; 56 (7): 551-4; Department of Clinical Research, National Sanyo Hospital, Ube, Japan.
SURGRX 510(K) Summary (# K031133); Palo Alto, CA; 5 pgs.; Jul. 3, 2003.
Tajiri M. et al.: Evaluation of an Ultrasonic Cutting and Coagulating System (Harmonic Scalpel) for Performing a Segmental and Wedge Resection of the Lung: Dec. 1998 Kyobu Geka.; 51 (13): 1116-9; Department of Surgery, Kan to Rosai Hospital, Kawasaki, Japan.
Tamussno. K. et al.: Electrosurgical Bipolar Vessel Sealing for Radical Abdominal Hysterectomy: Feb. 2005 Gynecol Oncol.: 96 (2): 320-2:Department of Obstetrics and Gynecology, Medical University of Graz, Auenbruggerplatz 14, A-8036 Graz, Austria. Karl.tamussino@meduni-graz.at.
The Gynecare Versapoint; All contents copyright © Johnson & Johnson Gateway, LLC, downloaded 2005, http://www.jnjgateway.com/homejhtml?loc=USENG&page=viewContent &contentId=edeaO.
Timor-Tritsch IE et al.: Transvaginal Ultrasound-Assisted Gynecologic Surgery: Evaluation of a New Device to Improve Safety of Intrauterine Surgery; Oct. 2003 Am J Obstet Gynecol.; 189 (4); 1074-9; Department of Obstetrics and Gynecology, New York University School of Medicine, NY 10016, USA. ilan.timor@med.nyu.edu.
Treat; A new thermal device for sealing and dividing blood vessels; http://www.starioninstruments.com/PDFs/Treat.pdf; downloaded Jun. 29, 2005; 2 pgs.
Tucker. R.D. et al.: Capacitive Coupled Stray Currents During Laparoscopic and Endoscopic Electrosurgical Procedures: Jul.-Aug. 1992: Biomedical Instrumentation & Technology vol. 26, No. 4 p. 303-11;; USA.
Tucker. RD et al.: Bipolar Electrosurgical Sphincterotomv: Gastrointest Endosc. Mar.-Apr. 1992; 38 (2): 113-7; Department of Pathology, University of Iowa Hospitals Clinics, Iowa City 52242.
TYCO Healthcare; The LigaSure Vessel Sealing System (Brochure); Apr. 2002; 8 pgs.
U.S. Patent Issued for Novare Surgical Systems Cygnet (R) Surgical Clamp; Novare Signs Multi-Year Supply Agreement With Boston Scientific; PR Newswire, pNA; Sep. 2, 2003.
Valley Forge Scientific Corp.—Company Report: Jan. 27, 1993: Investext. p. 1-1.
Valleylab Products—Electrosurgical Forceps: The Surgeon's Choice for Quality and Precision: htto://www.vallevlab.com/oroduct/es/accessories/forcepsover.html; © 2005 valleylab.
Valleylab Products—Ligasure TM Vessel Sealing System; http://www.valleylab.com/product/vessel_seal/index.html, © 2005.

(56) References Cited

OTHER PUBLICATIONS

Van Lue et al.; U.S. Appl. No. 13/110,848 entitled "Electrosurgical Tissue Sealing Augmented With a Seal-Enhancing Composition", filed May 18, 2011.
Walberg, Erik; U.S. Appl. No. 13/021,633 entitled "Laparoscopic radiofrequency surgical device," filed Feb. 4, 2011.
Weyl. BP: How to Increase the Proportion of Vaginal Hysterectomies-Bipolar Coagulation: Sep. 1999 Am J Obstet Gynecol.; 181 (3): 768.
Wilson. Fred: Cool Tool. Hot New Application: Radiofrequency Energy Removes Head, Neck Tumors. (Dermatologic Surgery): Aug. 2003; Dermatology Times, v. 24, n. 8, p. 54.
Zhi, Xu-Ting et al.; Management of Gastroesophageal Reflux Disease. Medications. Surgery. Or Endoscopic Therapy? (Current Status and Trends): 2005: Journal of Long-Term Effects of Medical Implants v. 15 n. 4 2005. p. 375-388g.
Japanese Office Action with English language translation for Application No. 2015-533711, dated Jun. 14, 2017, 6 pages.

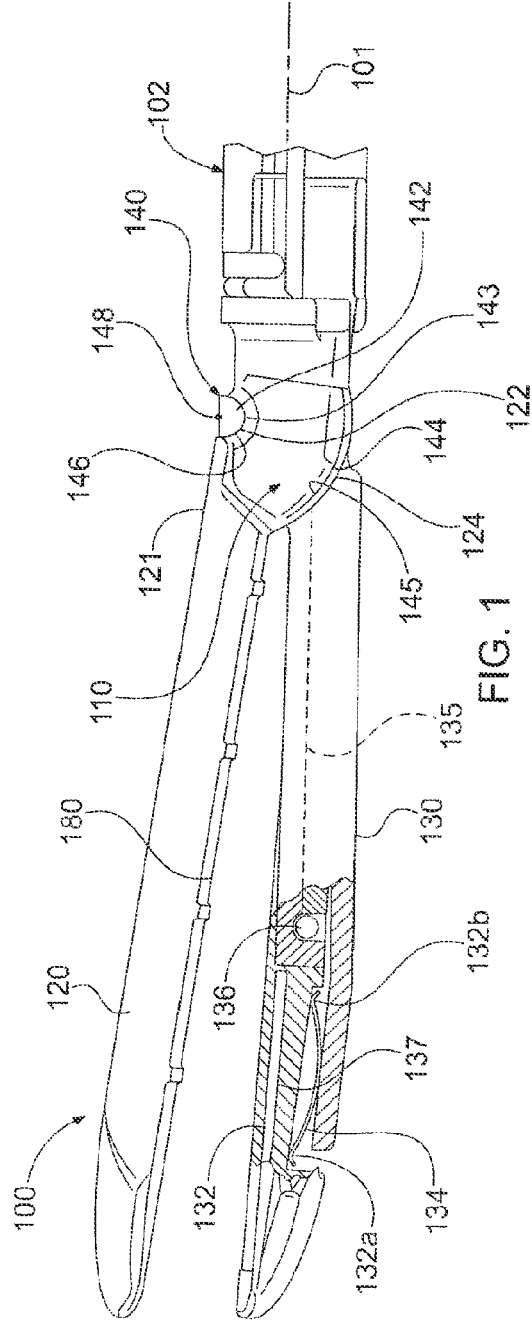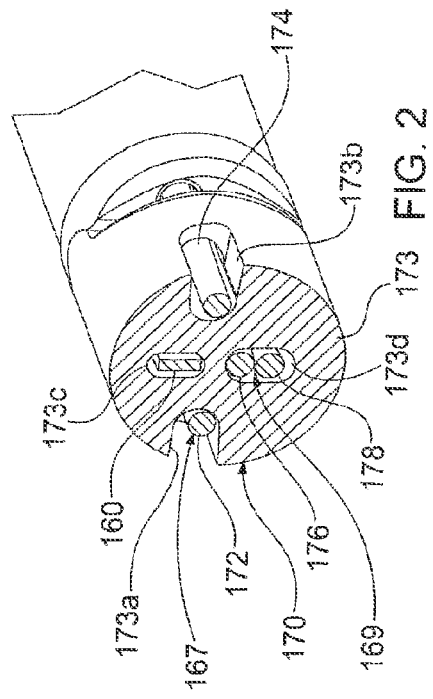

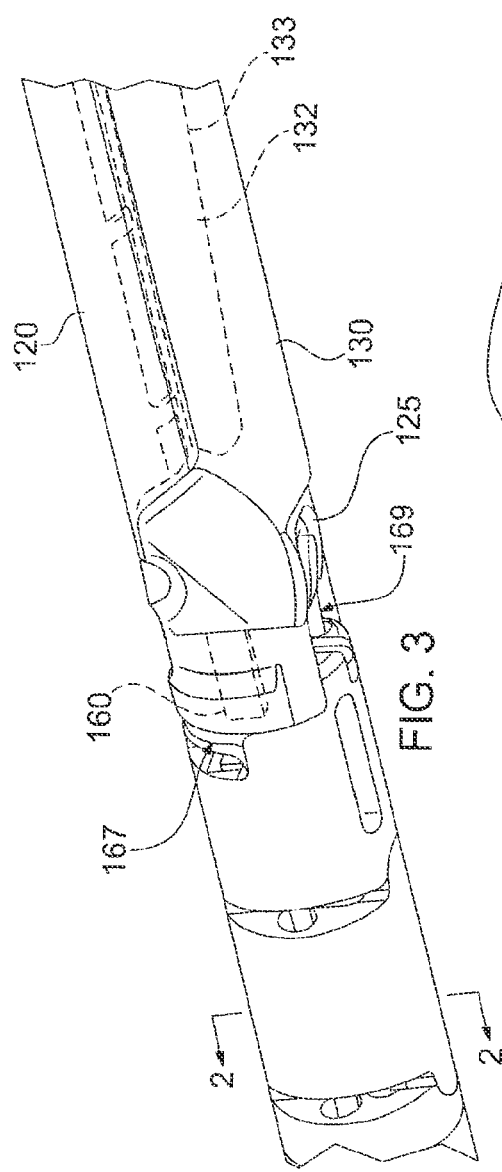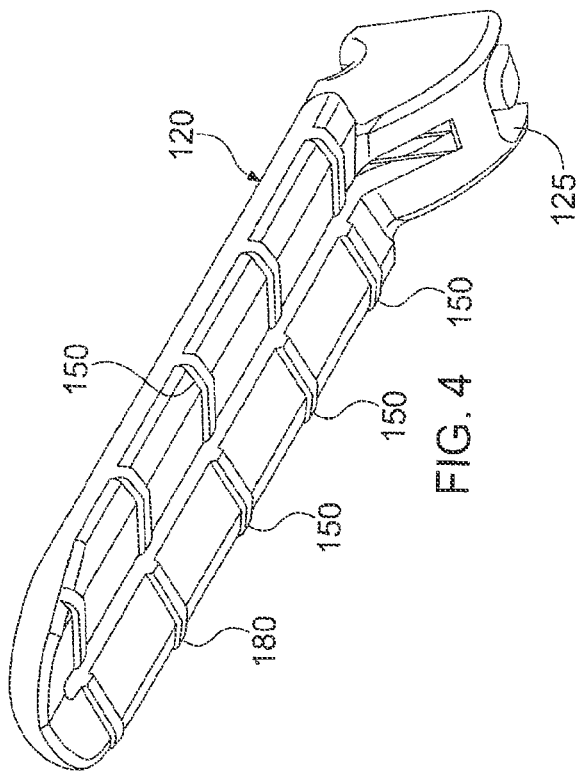

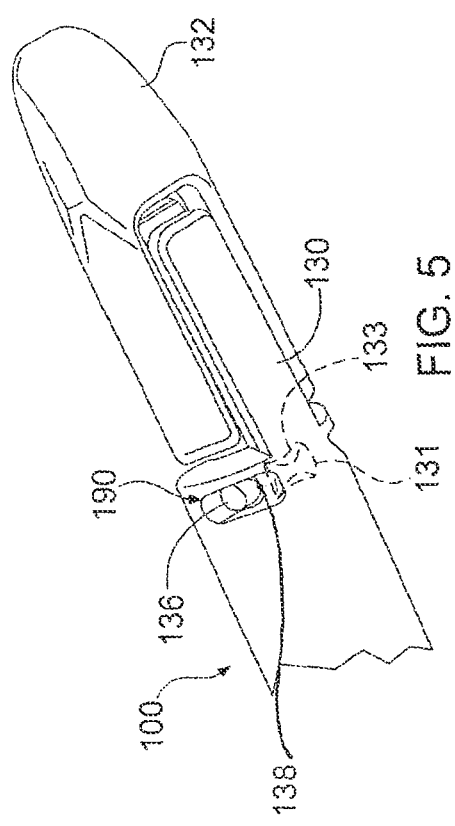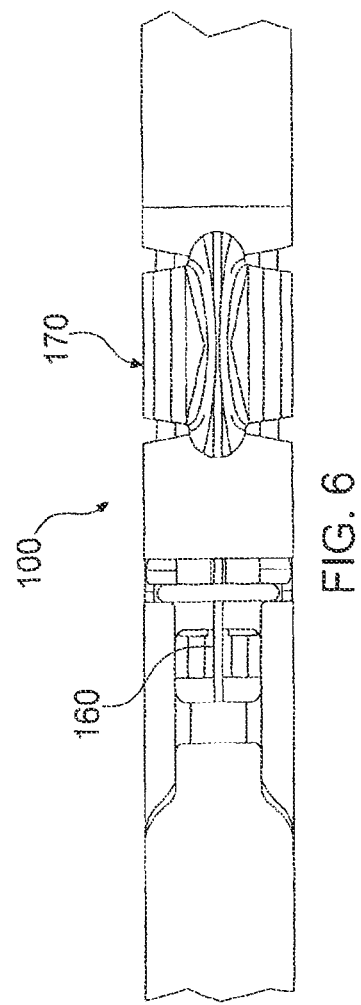

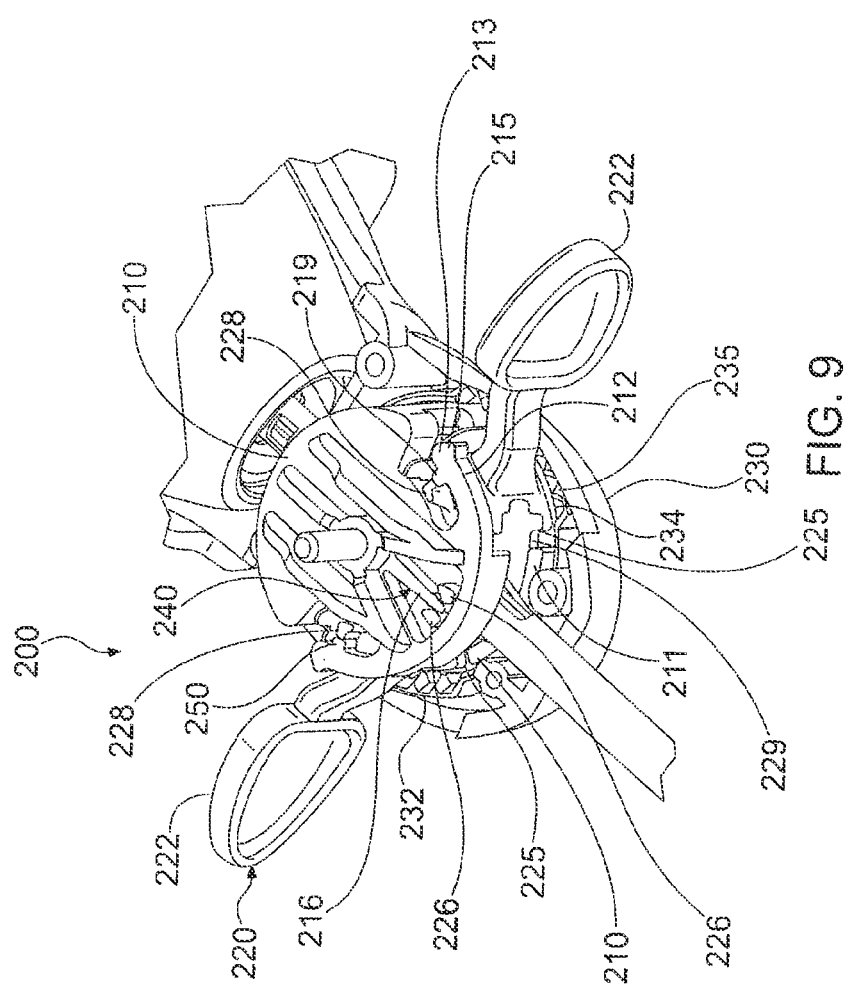

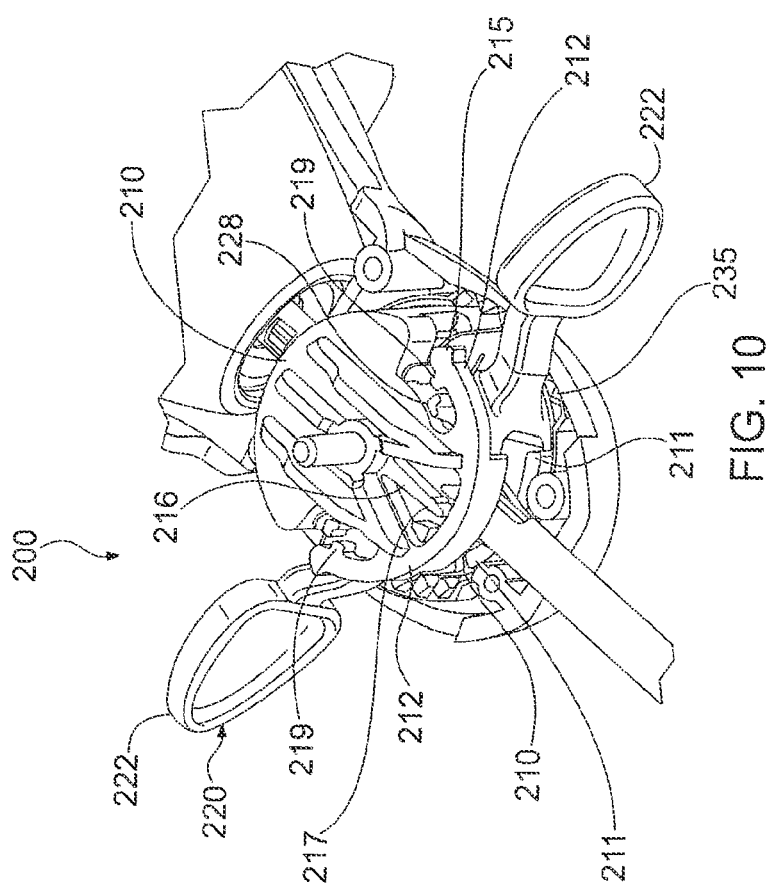

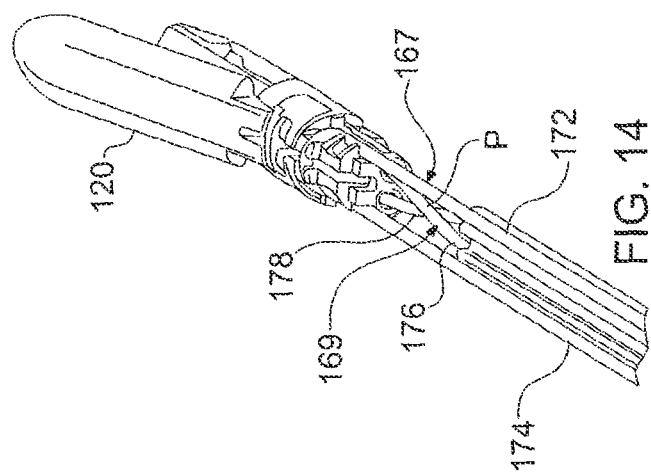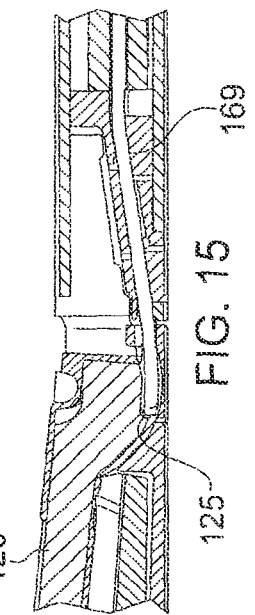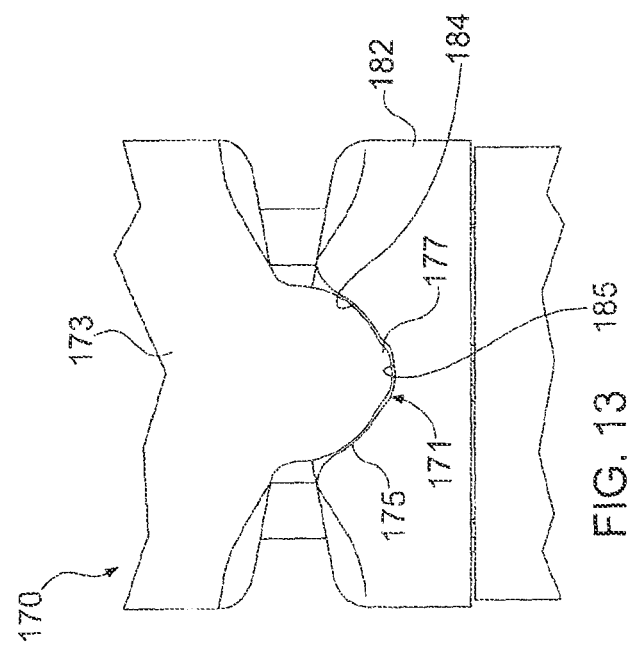

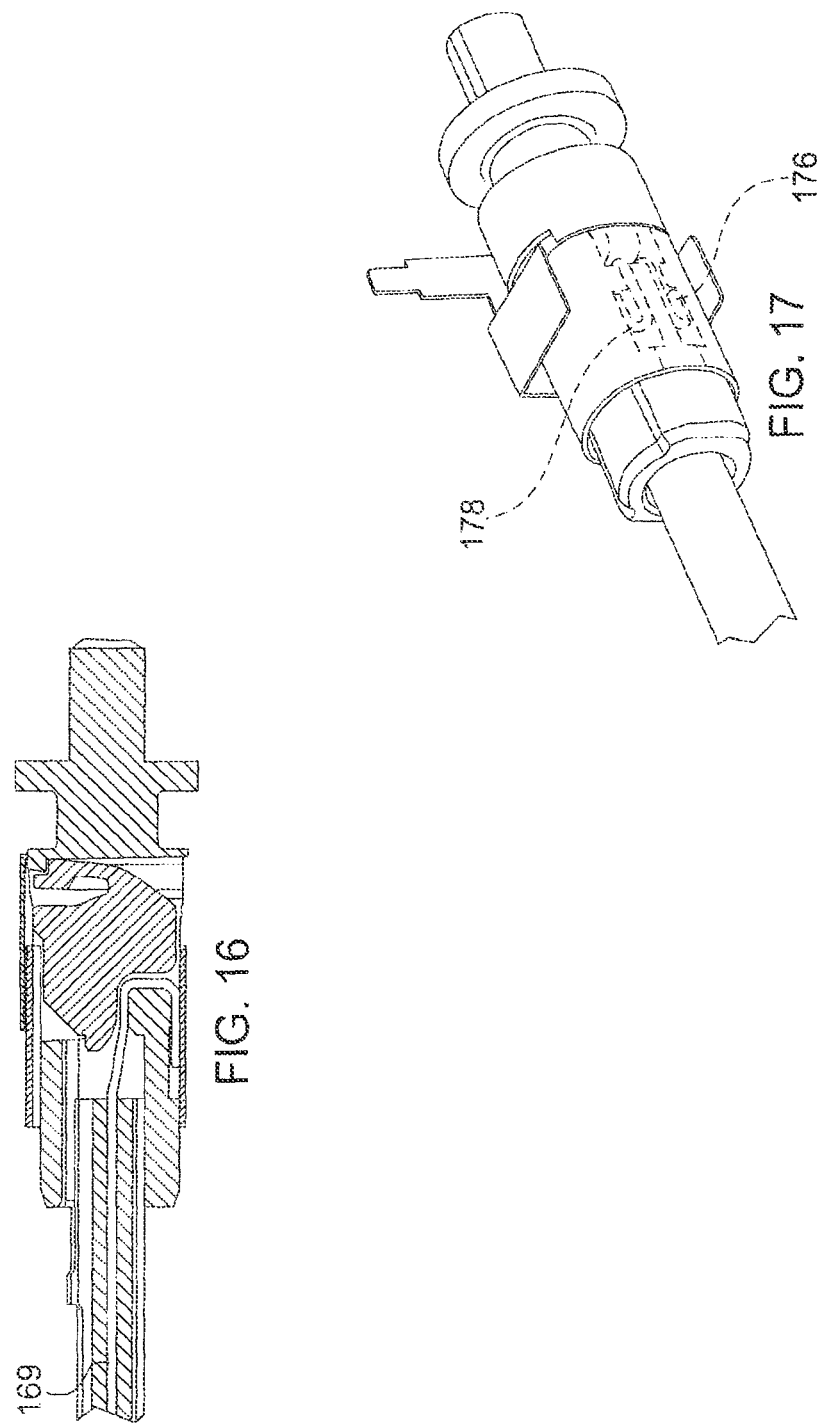

APPARATUS FOR TISSUE CUTTING AND SEALING

RELATED APPLICATIONS

This application is the U.S. national phase of international patent application number PCT/IB2013/002133, filed Sep. 26, 2013, which claims priority to U.S. provisional patent application No. 61/705,721, filed Sep. 26, 2012 The contents of both applications are incorporated by reference herein in their entirety and for all purposes.

FIELD

The present application generally relates to electrosurgical instruments having opposing jaws for cutting and sealing tissue, and more specifically to electrosurgical instruments with jaws having improved stiffness and compressive strength, and an improved articulation mechanism.

BACKGROUND

Biopolar electrosurgical instruments apply radiofrequency (RF) energy to a surgical site to cut, ablate, or coagulate tissue. A particular application of these electrosurgical effects is to seal blood vessels or tissue sheets. A typical instrument takes the form of a pair of opposing jaws or forceps, with one or more electrodes on each jaw tip. In an electrosurgical procedure, the electrodes are placed in close proximity to each other as the jaws are closed on a target site such that the path of alternating current between the two electrodes passes through tissue within the target site. The mechanical force exerted by the jaws and the electrical current combine to create the desired surgical effect. By controlling the level of mechanical and electrical parameters, such as the pressure applied by the jaws, the gap distance between electrodes, and the voltage, current, frequency, and duration of the electrosurgical energy applied to the tissue, the surgeon can coagulate, cauterize, or seal tissue toward a therapeutic end.

Electrosurgical procedures can be performed in an open environment, through conventional incisions, or using laparoscopic procedures. In laparoscopic procedures, the electrosurgical instrument must be able to fit through a cannula or trocar having a very small inner diameter that is typically between 5 mm and 10 mm. It is possible to make an electrosurgical instrument small enough to meet this size requirement. Nevertheless, the push to make instruments smaller often competes against other equally important design criteria.

The compression force exerted by the instrument is one of the most important design criteria that competes with instrument size. Ordinarily, a high compression force between the jaws is needed to form a proper seal within a reasonably short amount of time. Without sufficient compression force, the instrument may not be able to form a proper seal, or may form a proper seal only after a long time. It can be very difficult to create sufficient compression force with a smaller electrosurgical instrument because as the size of the instrument decreases, the percentage of space taken up by non-structural elements in the jaws increases. For example, the components that control tissue cutting, jaw actuation, articulation and power delivery all take up space in the jaws. Each component requires the removal of material from the jaws to provide space for the component. This reduces material mass and stiffness in the jaws, thereby reducing the compression force that can be created.

Based on the foregoing, there is a need for improved electrosurgical devices that can be reduced in size without sacrificing important parameters like compressive strength.

SUMMARY

According to one example of the invention, an electrosurgical device for cutting and sealing tissue includes an upper jaw located at a distal end of the electrosurgical device that opposes a lower jaw. The lower jaw is pivotally connected to the upper jaw by a pivot connection. The pivot connection includes a passage that contains a portion of the upper jaw. The upper jaw is axially displaceable through the passage to pivot the upper jaw relative to the lower jaw between a relatively open condition and a relatively closed condition. The upper jaw and lower jaw are operable in the relatively closed condition to deliver RF energy to tissue.

According to one aspect, the electrosurgical device for cutting and sealing tissue, the electrosurgical device comprises an upper jaw located at a distal end of the electrosurgical device and opposing a lower jaw, the lower jaw pivotally connected to the upper jaw by a pivot connection, wherein the pivot connection comprises a passage that contains a portion of the upper jaw, the upper jaw being axially displaceable through the passage to pivot the upper jaw relative to the lower jaw between a relatively open condition and a relatively closed condition, the upper jaw and lower jaw operable in the relatively closed condition to deliver RF energy to tissue.

According to another aspect of said electrosurgical device, the upper jaw is pivotable relative to the lower jaw about a pivot point located adjacent to an outside edge of the upper jaw, the pivot point being offset from a center line of the device.

According to yet another aspect of said electrosurgical device, the pivot connection comprises a semi-cylindrical element having a convex surface that engages a first side of the upper jaw.

According to yet another aspect of said electrosurgical device, the pivot connection further comprises a concave surface that engages a second side of the upper jaw.

According to yet another aspect of said electrosurgical device, the convex surface and the concave surface define opposing walls of the passage.

According to yet another aspect of said electrosurgical device, the convex surface and the concave surface follow circular profiles that are concentric about a common point.

According to yet another aspect of said electrosurgical device, said device is further comprising a lower jaw housing that contains the lower jaw, the lower jaw being positioned in a distal portion of the lower jaw housing.

According to yet another aspect of said electrosurgical device, the lower jaw is pivotally connected to the lower jaw housing by a lower jaw pivot connection.

According to yet another aspect of said electrosurgical device, the lower jaw pivot connection comprises a pin-less connection comprising a pair of bosses projecting outwardly from the lower jaw, the bosses engaging a pair of apertures in lower jaw housing.

According to yet another aspect of said electrosurgical device, said device is further comprising a lower jaw spring positioned between the lower jaw housing and the lower jaw.

According to yet another aspect of said electrosurgical device, the lower jaw spring is located at a distal portion of the lower jaw, the lower jaw spring biasing a distal portion of the lower jaw towards the upper jaw.

According to yet another aspect of said electrosurgical device, the upper jaw comprises a plastic skin molded over the upper jaw to electrically isolate the upper jaw from the lower jaw.

According to yet another aspect of said electrosurgical device, said device is further comprising a wrist section between an elongated shaft of the electrosurgical device and the upper and lower jaws, the upper and lower jaws being displaceable at the wrist section to allow the upper and lower jaws to bend relative to the elongated shaft.

According to yet another aspect of said electrosurgical device, said device is further comprising an articulation wire looped through a passage in the wrist section.

According to yet another aspect of said electrosurgical device, power is delivered to the upper and lower jaws through the articulation wire.

According to yet another aspect of said electrosurgical device, the wrist section comprises a vertebra, a bushing and a self-straightening coupling between the vertebra and bushing to urge the upper and lower jaws toward a centered position.

According to yet another aspect of said electrosurgical device, the device is further comprising an actuation wire looped through a passage in one of the upper and lower jaws.

According to yet another aspect of said electrosurgical device, the actuation wire comprises a first actuation wire section and a second actuation wire section, the first actuation wire section crossing over the second actuation wire section so that the first and second actuation wire sections exert equal forces on said one of the upper and lower jaws through which the actuation wire is looped.

According to yet another aspect of said electrosurgical device, power is delivered to the upper and lower jaws through the actuation wire.

According to yet another aspect of said electrosurgical device, the upper jaw comprises a first mating surface and the lower jaw comprises a second mating surface that mates with the first mating surface, the first and second mating surfaces each comprising a V-shaped contour.

According to yet another aspect of said electrosurgical device, the device is further comprising an articulation mechanism for controlling bending or turning motion of the upper and lower jaws.

According to yet another aspect of said electrosurgical device, the articulation mechanism comprises a housing and an indexing disk rotatably displaceable in the housing.

According to yet another aspect of said electrosurgical device, the housing comprises a plurality of ratchet notches, and the indexing disc comprises an indexing arm for engaging the ratchet notches to index the position of the upper and lower jaws.

According to yet another aspect of said electrosurgical device, the articulation mechanism comprises an automatic locking mechanism that prevents external force on the upper and lower jaws from moving the upper and lower jaws out of an indexed position.

BRIEF DESCRIPTION OF THE DRAWINGS

The foregoing summary and the following detailed description will be better understood in conjunction with the drawing figures, of which:

FIG. 1 is a truncated perspective view of an electrosurgical device in accordance with one embodiment;

FIG. 2 is a truncated perspective view of electrosurgical device components that can be used in the embodiment of FIG. 1 or other embodiments;

FIG. 3 is another truncated perspective view of electrosurgical device components that can be used in the embodiment of FIG. 1 or other embodiments;

FIG. 4 is another truncated perspective view of electrosurgical device components that can be used in the embodiment of FIG. 1 or other embodiments;

FIG. 5 is another truncated perspective view of electrosurgical device components that can be used in the embodiment of FIG. 1 or other embodiments;

FIG. 6 is another truncated perspective view of electrosurgical device components that can be used in the embodiment of FIG. 1 or other embodiments;

FIG. 9 is another truncated perspective view of electrosurgical device components that can be used in the embodiment of FIG. 1 or other embodiment, showing components of an articulation mechanism, with some components removed for clarity;

FIG. 10 is another truncated perspective view of the components of FIG. 9, with some components removed for clarity;

FIG. 13 is a plan view of a pivot interface between components that can be used in the embodiment of FIG. 1 or other embodiments;

FIG. 14 is a truncated perspective view of an electrosurgical device with components removed to show the configuration of internal components that can be used in the embodiment of FIG. 1 or other embodiments;

FIG. 15 is an enlarged truncated partial cross section view of an electrosurgical device showing the configuration of internal components that can be used in the embodiment of FIG. 1 or other embodiments;

FIG. 16 is another enlarged truncated partial cross section view of an electrosurgical device showing the configuration of internal components that can be used in the embodiment of FIG. 1 or other embodiments; and FIG. 17 is a truncated perspective view of an electrosurgical device showing the configuration of internal components that can be used in the embodiment of FIG. 1 or other embodiments.

DETAILED DESCRIPTION

Figure 8:
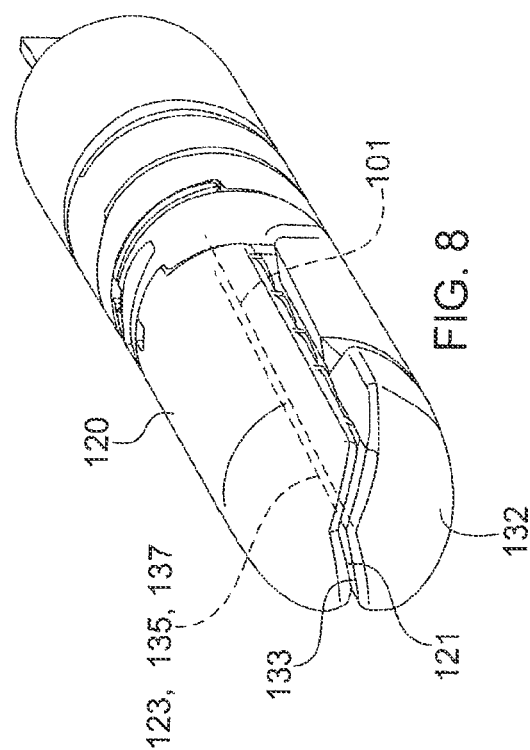
FIG. 8 is another truncated perspective view of electrosurgical device components that can be used in the embodiment of FIG. 1 or other embodiments.

Applicants have developed improved electrosurgical devices that address the need for reduced size, while also addressing the need for high compression force between the jaws. The improved electrosurgical devices were designed using a holistic approach that eliminates, simplifies, or combines individual components where appropriate, while maximizing strength and stiffness in the jaws.

The following examples illustrate features that are designed to address the competing needs for reduced size and for stronger stiffer jaws. Although different features will be described and shown on an electrosurgical device 100, many of the features are independent features. Some or all of these features can appear on the same device, but need not be on the same device, and can be used in different combinations on different embodiments of the invention. Devices in accordance with the invention may include many of the device features and characteristics shown and described in U.S. application Ser. Nos. 12/027,231 and 13/070,391, the contents of which are incorporated by reference herein in their entirety.

Pivot Connection

Referring to FIG. 1, an electrosurgical device 100 is shown in accordance with one exemplary embodiment. Device 100 includes an elongated shaft 102. Elongated shaft 102 has a distal end portion 110 that features an upper jaw 120 and a lower jaw housing 130. Lower jaw housing 130 contains a lower jaw 132. A cutting blade 160, shown in FIGS. 2 and 3, is displaceable between the upper and lower jaws 120 and 132 to cut tissue.

Upper jaw 120 and lower jaw housing 130 are pivotally joined by a pivot connection 140 that allows the upper jaw to pivot relative to the lower jaw housing to open and close the upper jaw. Pivot connection 140 includes a semi-cylindrical element 142 having a convex surface 143 that engages a first side 122 of upper jaw 120. Pivot connection 140 also includes an arc-shaped concave surface 144 that engages a second side 124 of upper jaw 120. Convex surface 143 and concave surface 144 follow circular profiles that are concentric about a pivot point 148. Semi-cylindrical element 142 and concave surface 144 are separated from one another by an arcuate passage 145. The edges of arcuate passage 145 form a track or chute 146 through which the upper jaw 120 slides. The arcuate shape of track 146 causes the upper jaw 120 to pivot relative to lower jaw housing 130 as the upper jaw slides through the passage. Upper jaw 120 pivots about pivot point 148.

As can be seen in FIGS. 1 and 3, pivot connection 140 differs from conventional pin connections in significant ways. As an initial matter, pivot connection 140 does not require the removal of material from the jaws. Upper jaw 120 fits into the body of lower jaw housing 130 through arcuate passage 145, with little or no void space in or around the upper jaw and lower jaw housing. Conventional pin connections, in contrast, require the removal of material to accommodate the pin and to allow each jaw to pivot relative to one another. Removal of material from the jaws reduces the mass of the jaws, and consequently, the amount of stiffness and compression force that can be exerted on tissue when the jaws are closed.

Pivot connection 140 also differs from conventional pin connections with regard to the position of the pivot connection relative to the jaws. Pin connections are typically located along the midline of the instrument between the upper and lower jaws. Pivot point 148, in contrast, is offset from a center line 101 of the device, adjacent to the outside edge 121 of upper jaw 120. This offset arrangement has an advantage over cross pin connections located on the midline because it provides a clear unobstructed path through the midline. The unobstructed path allows cutting blade 160 to travel along the midline between the blades, without any obstruction created by a pin.

Electrode Configuration

The electrode configuration in device 100 is another feature that balances the need for reduced size and increased jaw stiffness. Many known electrosurgical devices use one or more stand-alone electrodes placed on the jaws. Stand-alone electrodes require space to capture, isolate and house the electrodes in the jaws, sacrificing stiffness in the jaws. To address this problem, device 100 is designed without stand-alone electrodes. Power is is delivered directly to upper jaw 120 and lower jaw housing 130.

Power Delivery

Known electrosurgical devices deliver power to electrodes using dedicated power transmission wires that extend through the jaws. In many cases, these dedicated power transmission wires are in the form of stationary braided or jacketed wires. Dedicated power transmission wires occupy a significant amount of space and require throughbores, passages, etc. that remove material from the jaws. As such, dedicated power transmission wires and their throughbores decrease jaw stiffness, thereby reducing the amount of compressive force that can be applied between the jaws during sealing. Dedicated power transmission wires can also limit movement of the instrument in cases where the dedicated wires do not have sufficient slack or elasticity to move or stretch as the instrument moves.

To preserve stiffness in the jaws and provide greater instrument mobility and flexibility, devices in accordance with the invention preferably include multifunctional components that control both motion and power delivery. Dedicated power transmission wires that sacrifice jaw stiffness and instrument mobility are preferably avoided. Energy delivery can be provided through the same components that control actuation and/or articulation, for example. Energy delivery can also be provided through translating components.

Referring to FIG. 2, a cross section of device 100 is shown at the "wrist" or "vertebra" section 170. Wrist section 170, which is described in more detail in a later section, includes a vertebra 173 that is substantially solid, with the exception of four through-passages. Two through passages accommodate a looped articulation wire 167, and one through passage accommodates a looped actuation wire 169. Articulation wire 167 is operable to allow distal end portion of the device to bend relative to the longitudinal axis of the device. Actuation wire 169 is operable to open and close upper jaw 120. Articulation wire 167 is looped through the passages, forming two generally parallel articulation wire sections 172 and 174. Similarly, actuation wire 169 is looped through the passages, forming two generally parallel actuation wire sections 176 and 178. Actuation wire sections 176 and 178 cross over one another at the section shown in FIG. 2, as will be explained in more detail. FIGS. 3 and 14 show how articulation wire 167 and actuation wire 169 are routed through a distal end portion of the device, with a looped end of the articulation wire visible.

A first through-passage 173a located in an outer peripheral section of vertebra 173 contains the first articulation wire section 172. A second through-passage 173b located in another outer peripheral section of vertebra 173 contains the second articulation wire section 174. A third through-passage 173c located in an interior section of vertebra 173 contains cutting blade 160. A fourth through-passage 173d located in an interior section of vertebra 173 contains actuation wire sections 176 and 178.

Power is delivered to upper jaw 120 through actuation wire 169. Power is delivered to the lower jaw housing 130 through articulation wire 167, and may also be delivered through any other series of metal components, including jaw bushings, vertebra or shafts that may be metal and that contact each other in series, and which are isolated from actuation wire 169. Lower jaw housing 130 and lower jaw 132 both include metal surfaces in contact with one another, so that power delivered to the lower jaw housing is conducted to the lower jaw.

Isolation

Surfaces on upper jaw 120 that interface with lower jaw housing 130 and lower jaw 132 must be electrically isolated. To address this, device 100 includes a plastic skin 180 over upper jaw 120. Upper jaw 120 is over-molded with the plastic skin 180 to isolate the surfaces that interface with lower jaw housing 130. The over-mold does not require clearance between components, preserving space to allow the jaws to have more material mass. Over-molding upper jaw 120 also allows offsetting features to be created on the upper jaw, as will be explained in the next section.

Gap Generating Offset Features

The over-molded skin 180 has multiple functions. A first function of the over-molded skin is to electrically isolate upper jaw 120 from lower jaw housing 130, as described above. A second function of the over-molded skin is to generate offsetting features that create a gap space between the electrodes, i.e. upper jaw 120 and lower jaw 132, when the jaws are closed. In FIG. 4, an embodiment of the device includes offsetting features shown in the form of straps 150 that extend transversely across upper jaw 120. Straps 150 are produced during the over-mold process. A third function of the over-molded skin is to reduce the temperature of the back side of the jaw that comes into contact with the tissue, so as to reduce the risk of tissue burning.

Gap generating offset features in accordance with the invention need not take the form of transverse straps, and can be any surface irregularity or projection that provides a separation between electrodes when the jaws are closed. For example, upper jaw 120 may include a plurality of holes that receive rivets or rivet-like members that project from the surface of the upper jaw and contact lower jaw 132.

Pin-Less Lower Jaw

The lower jaw 132 is pivotally connected to lower jaw housing 130 by a lower jaw pivot connection 190. Pivot connection 190 between lower jaw 132 and lower jaw housing 130 represents one of the most critical areas where stiffness and strength must be maximized in the lower jaw to provide sufficient compression force. Pin connections and throughbores require removal of material from the lower jaw, reducing jaw stiffness and strength, as described above. Therefore, pivot connection 190 features a "pin-less" connection in the form of a pair of bosses 136. Bosses 136 project outwardly from lower jaw 132 and snap into small apertures 138 in lower jaw housing 130. With this arrangement, no material is removed from lower jaw 132 across the width of the jaw at the location of pivot connection 190.

As an alternative to bosses and apertures, lower jaw housing 130 can be lightly crimped to create a pivoting interface between the lower jaw housing and lower jaw 132.

Referring to FIG. 5, jaw 132 has a rounded convex bottom surface 133, and lower jaw housing 130 has a rounded concave inside surface 131. Concave inside surface 131 bears against convex bottom surface 133 when lower jaw housing 130 is pivoted relative to upper jaw 120. As such, concave inside surface 131 and convex bottom surface 133 form bearing surfaces that absorb compression force between lower jaw 132 and lower jaw housing 130 and direct the compression force away from the bosses 136 and apertures 138. Consequently, the structural integrity of lower jaw 132 does not depend greatly on the strength of bosses 136 or pivot connection 190.

Actuation Wire

One of the challenges of an articulating device is transmitting motion through the articulating members. When the device bends, the arc length through the joint changes as you move away from centerline. This generally requires the use of tall (for strength) and thin (for flexibility) actuation members which move along the centerline of the device. Articulation left and right prevents the use of short and flat actuation members or paired wire members arranged perpendicular to the articulation plane, because the members or wires will buckle and/or transmit motion and force unequally.

Device 100 uses an actuation wire 169 that is looped to form a pair of parallel wire sections 176 and 178, as noted above. Actuation wire sections 176 and 178 are configured to pivot the upper jaw 120 relative to lower jaw housing 130 when force is applied through the actuation wire sections. Looped actuation wire 169 is connected to a pin (not shown) in upper jaw 120. To pivot upper jaw 120 to an open position, a pushing force (or force directed toward distal end portion 110) is applied to the upper jaw through actuation wire sections 176 and 178. To pivot upper jaw 120 to a closed position, a pulling force (or tension force directed away from the distal end portion 110) is applied to the upper jaw through actuation wire sections 176 and 178. Each of the actuation wire sections 176 and 178 is set out from the centerline of the articulation plane, but in an arrangement that allows the wires to push or pull equally left to right. The solution is to twist the wires 180 degrees, crossing in the middle of the articulation members at a cross-over point P.

Figure 7:
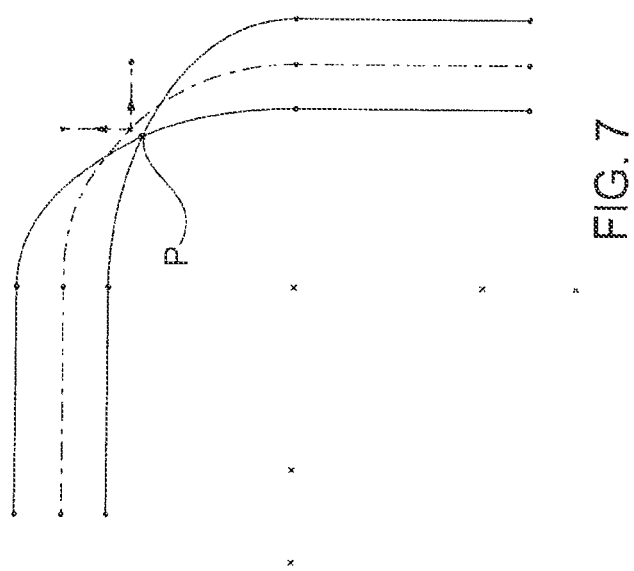
FIG. 7 is a schematic diagram illustrating arcs that correspond to arc lengths of actuation wires in a cross configuration that may be used in the embodiment of FIG. 1 or other embodiments.

FIG. 2 is a cross section view of device 100 taken through a plane that intersects the cross-over point P, where actuation wire section 176 crosses over actuation wire section 178. FIG. 14 is a perspective view of the distal end of device 100, with components removed to show how wire section 176 crosses over wire section 178 at point P. FIG. 15 is a cross section view of device 100 that shows how actuation wire 169 connects with upper jaw 120. Actuation wire 169 is looped through a U-shaped slot 125 formed in a base portion of upper jaw 120. FIGS. 16 and 17 are cross section views of device 100 that show how actuation wires 176 and 178 connect with the proximal end of the device. The cross-over of actuation wires 176 and 178 results in arc lengths through the articulation region that are mirror images of each-other and remain the same length. The arc lengths are illustrated schematically in FIG. 7. The crossover point P acts like a pivot point for the wires. By maintaining equal arc lengths, the forces are balanced between the actuation wire sections 176 and 178, even when the actuation wire sections are bent during articulation of the jaws, so that the wire sections pull evenly on the upper jaw and pose minimal resistance to the articulation wires 172 and 174. Articulation wire sections 172 and 174 are maintained in a state of tension so that the components of the system are kept together in tension, allowing the jaws to open and close properly and to allow the distal end of the device to articulate properly.

Jaw Contour

Referring to FIG. 8, upper jaw 120 has a mating surface 131 that mates with lower jaw 132. Lower jaw 132 similarly has a mating surface 133 that mates with upper jaw 120. Mating surfaces 131 and 133 each have a V-shaped contour as shown that provides several advantages over planar mating surfaces.

The V-shaped contour provides a self-alignment feature that keeps upper jaw 120 and lower jaw 132 aligned with one another. The self-alignment feature eliminates the need for long component lengths and tight tolerance geometry behind the jaws to control alignment. The V-shaped mating surfaces 131 and 133 also have larger surface areas than planar surfaces, resulting an incrementally wider area to engage tissue.

The axial center line 123 of mating surface 131 meets the axial center line 135 of mating surface 133 along a line 137 that is offset from a center line 101 of the device 100. In this arrangement, the cutting plane 103 can be moved away from center line 101 of device 100, allowing cutting blade 160 to be located away from the center so that other components can be positioned toward the center of the device.

Lower Jaw Spring

Referring back to FIG. 1, lower jaw housing 130 contains a lower jaw spring 134 between the lower jaw housing and lower jaw 132. Lower jaw spring 134 bears against the inside of lower jaw housing 130 to pivot lower jaw 132. In this configuration, lower jaw spring 134 biases a distal portion 137 of lower jaw 132 towards upper jaw 120.

Known electrosurgical devices that include lower jaw springs place the spring at a proximal section of the lower jaw, at a point located proximally with respect to the pivot point. To provide room for the spring, a certain amount of material is removed from the proximal portion of the lower jaw, and/or from the lower jaw housing in a similar area. This removal of material can create a substantial decrease in strength and stiffness at the proximal section of the lower jaw and/or lower jaw housing. Jaw strength and stiffness are especially important at the proximal section of the lower jaw and jaw housing because the proximal section is a critical area for providing compressive force. FIG. 1 shows the relative thickness of the lower jaw 132 at its proximal section 135 and its distal section 137.

To avoid losing jaw strength and stiffness at the proximal portion 135 of lower jaw 132, lower jaw spring 134 is located at distal portion 137 of the lower jaw. This preserves more mass around proximal section 135 where it is needed. Distal section 137 of lower jaw 132 has more mass to begin with than proximal section 135, and is therefore more suited for accommodating lower jaw spring 134.

Lower jaw spring 134 frictionally engages lower jaw 132 in two places, 132a and 132b. This engagement at two locations assists in transferring energy from lower jaw housing 130 to lower jaw 132.

Articulation Mechanism

FIGS. 9-12 show an articulation mechanism 200 in accordance with the invention. Articulation mechanism 200 controls bending or turning motion at wrist section 170, which permits the upper jaw 120 and lower jaw 132 to bend left or right. More specifically, articulation mechanism 200 is operable to apply a tension force to one of the articulation wire sections 172 and 174 to bend the device at wrist section 170.

Articulation mechanism 200 includes a pair of indexing disks 210 that hold the articulated position of the upper and lower jaws 120 and 132. Articulator mechanism 200 also includes an articulator 220 operable to rotate the indexing disks 210. Articulator 220 has a pair of handles 222 that extend outwardly from the indexing disks. Handles 222 and indexing disks 210 are rotatably displaceable in a housing 230. Housing 230 has an interior wall 232 lined with ratchet notches 234. Each indexing disk 210 has a pair of indexing arms 212 operable to engage and disengage ratchet notches 234 when the indexing disk is rotated in housing 230. Ratchet notches 234 are separated from one another by a series of inwardly pointing ratchet teeth 235. Each indexing arm 212 has a distal end 213 with a pointed tip 215 configured to slidably interact and engage with ratchet notches 234 and ratchet teeth 235 as indexing disks 210 rotate in the housing. Indexing arms 212 are formed of resilient flexible material that allows the indexing arms to flex or bend radially inwardly toward the center of indexing disks 210 in response to contact between tip 215 and indexing teeth 235. When tips 215 engage the inner most sections of ratchet teeth 235, indexing arms 212 bend inwardly under stored energy. As indexing disks 210 rotate and the tips 215 align with ratchet notches 234, indexing arms 212 snap outwardly and return to a relaxed state with the tips positioned in the ratchet notches.

Articulation mechanism 200 includes a centering mechanism 240 that biases articulator 220 to a centered or "neutral" condition. The neutral condition is shown in FIG. 9. Centering mechanism 240 includes a pair of flexible leaf springs 216 that extend from each indexing disk 210. Each leaf spring 216 has a distal end 217 that is held in a captive position between a pair of projections 226 on articulator 220. When articulator 220 is in the neutral condition, each leaf spring 216 is substantially straight, in a relaxed state. When articulator 220 begins to rotate left or right, projections 226 also rotate, but the indexing disks 210 do not rotate immediately, and instead remain stationary, as will be explained in more detail below. As such, each leaf spring 216 bends in response to initial movement of the projections 226, storing energy in the leaf spring that creates a biasing force. The biasing force in each leaf spring 216 applies force to articulator 220 in the direction opposite of the direction in which the articulator was rotated, to urge the articulator back toward the neutral condition. When rotation force is released from articulator 200, the biasing force in leaf springs 216 returns articulator 200 back to the neutral condition.

Articulation mechanism 200 further includes an automatic locking mechanism 250. Locking mechanism 250 is a passive interlock mechanism that prevents external force on the upper and lower jaws 120 and 132 from moving the jaws out of their indexed position. Locking mechanism 250 includes four detents 228 on articulator 220, two of which are visible in the Figures, and two which are on the opposite side of the articulator. Each detent 228 is movable with respect to indexing disks 210 between a locking position and a release position. In the locking position, shown in FIG. 9, each detent 228 is aligned with an inner projection 219 on one of the indexing arms 212. In this position, inner projections 219 block the indexing arms and prevent them from bending inwardly, thereby preventing the indexing arms from disengaging the ratchet notches and precluding articulation of the jaws from their indexed position. In the release position, shown in FIG. 10, each detent 228 is rotated out of alignment with the corresponding inner projection 219, allowing the indexing arms to bend inwardly and disengage the ratchet notches to facilitate articulation of the jaws to another position.

In this arrangement, articulation mechanism 200 is a floating mechanism that is biased toward the neutral condition with respect to the indexing disks. In operation, the jaws are articulated by rotating articulator 220 either clockwise or counterclockwise relative to housing 230 via the handles 222. When rotation force is initially applied to handles 222, the applied force is opposed by the centering forces of leaf springs 216. If the applied force is greater than the centering forces, articulator 220 will rotate relative to indexing disks 210 so that the detents 228 move out of the locking position to the release position.

Articulator 220 has four abutment edges 225, and indexing disks 210 have corresponding abutment edges 211. When articulator is in the neutral condition, abutment edges 211 are spaced apart from abutment edges 225, creating small gaps 229 that define limits of travel. Upon initial rotation of handles 222, articulator 220 will rotate, and two of the abutment edges 225 will approach corresponding abutment edges 211 on indexing disks 210. After handles 222 are rotated through a small threshold angle of rotation, such as 5 degrees, the abutment edges 225 approaching the abutment edges 211 on indexing disks 210 will reach their limit of travel and contact the indexing disks 210. At this point, rotational force applied to the handles will be transferred to indexing disks 210 and rotate the indexing disks in tandem with articulator 220. As indexing disks 210 rotate, the tips 215 of indexing arms 212 bend inwardly as they slidably engage ratchet teeth 235 and snap outwardly as they align with ratchet notches 234 in the next indexed position. Upon reaching a desired indexed position, rotation force is released from handles 222, so that leaf springs 216 return articulator 220 to the neutral condition, with detents 228 returned to the locking position. In the locking position, detents 228 prevent indexing arms 212 from disengaging ratchet notches 234, effectively locking articulation wires 172 and 174 and wrist 170 in the indexed position.

Figure 11:
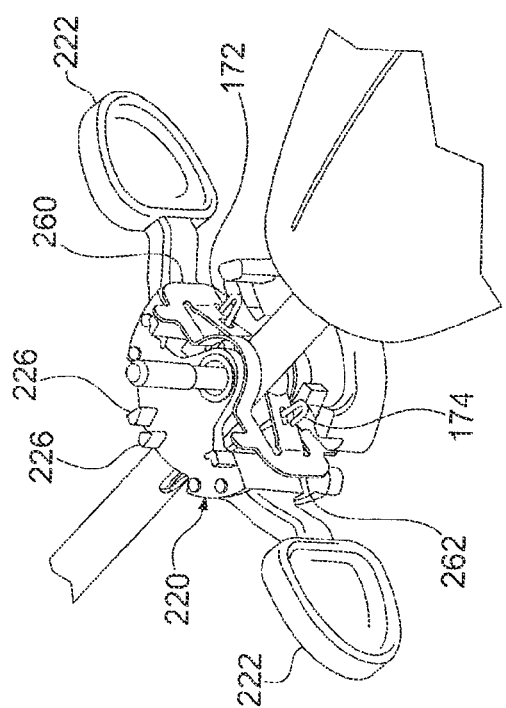
FIG. 11 is another truncated perspective view of the components of FIG. 9, with some components removed for clarity.
Figure 12:
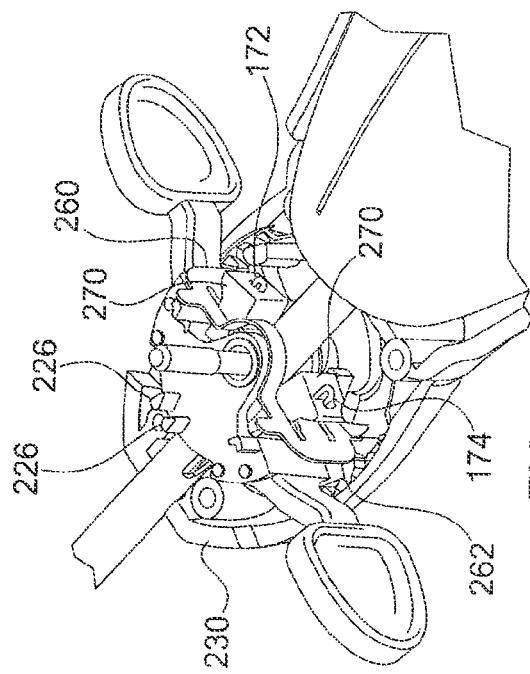
FIG. 12 is another truncated perspective view of the components of FIG. 9, with some components removed for clarity.

Referring to FIGS. 11 and 12, device 100 includes a spring plate 260 which is attached to proximal ends of articulation wires 172 and 174. Spring plate 260 places articulation wires 172 and 174 in tension to secure components in wrist 170 together, thereby avoiding the need to use other means to physically join the wrist components. Indexing disks 210 hold spring plate 260 in place in housing 230. Each articulation wire 172 and 174 extends through a hole in a wing portion 262 of spring plate 260. The proximal end of each articulation wire 172 and 174 is bent and captured in a wire stopper 270. Each wire stopper 270 is keyed to maintain its orientation against spring plate 260. Each wing portion 262 has a relaxed state in which the wing portion is bent in a proximal direction with respect to the rest of the spring plate 260. In the assembled state, the wire stoppers 270 are pulled distally against wing portions 262 to tension the articulation mechanism 200.

Wrist Mechanism

Embodiments may include a wrist mechanism with components having "non-circular" pivot interfaces. For example, the pivot interfaces between components may have parabolic, stepped or V-notched geometries, resulting in a moving axis of rotation rather than a traditional fixed axis of rotation associated with strictly "circular" geometries, such as spherical or cylindrical interfacing geometries. The moving axis of rotation provides the benefit of a self-straightening or self-centering coupling in which the adjoined vertebrae are urged to return to a straight configuration after being articulated. This bias toward a straightened configuration stabilizes the position of the jaws and provides resistance against jogging when the jaws are locked or contacting other objects.

The non-circular interface also combats the loss of compression force exhibited by the jaws when the jaws are articulated by lengthening the effective shaft length. In devices which have a "pull" type mechanism to close the jaws, lengthening the shaft (without changes in the jaw locking mechanism) will result in pulling harder for more compression force.

FIG. 13 shows one example of a non-circular interface 171 between vertebra 173 and a bushing 182 in wrist section 170. Non-circular interface 171 includes a rounded convex mating surface 175 on vertebra 173, and a rounded concave mating surface 184 on bushing 182. A step or "lobe" 177 extends outwardly from convex mating surface 175. The surface transitions between lobe 177 and convex mating surface 175 are rounded, forming a smooth compound curvature along the edge of vertebra 173. A recess 185 extends into concave mating surface 184 and has a shape that conforms to the geometry of lobe 177 as shown.

When wrist section 170 is straight (i.e. when the vertebrae are not articulated and the jaws are straight), convex mating surface 175 and lobe 177 are in phase with concave mating surface 184 and recess 185, with the lobe nested in the recess. When wrist section 170 is articulated, convex mating surface 175 and lobe 177 are shifted out of phase with concave mating surface 184 and recess 185, such that the lobe moves out of the recess and engages the concave mating surface. In this condition, the distance between vertebra 173 and bushing 182 is incrementally increased, shifting the axis of rotation between the parts. The dimension of lobe 177 may be very small relative to the size of convex mating surface 175. The rounded perimeter of lobe 177 may project as little as 0.002 inches from convex mating surface 175. Smaller or larger lobe configurations may also be used.

While preferred embodiments of the invention have been shown and described herein, it will be understood that such embodiments are provided by way of example only. Numerous variations, changes and substitutions will occur to those skilled in the art without departing from the invention. Accordingly, it is intended that the appended claims cover all such variations as fall within the scope of the invention.

What is claimed:

1. An electrosurgical device for cutting and sealing tissue, the electrosurgical device comprising:
   an upper jaw located at a distal end of the electrosurgical device;
   a lower jaw opposing the upper jaw; and
   a pivot connection that pivotally connects the upper jaw to the lower jaw,
   wherein the pivot connection comprises a first passage that contains a portion of the upper jaw, the upper jaw being axially displaceable through the first passage to pivot the upper jaw relative to the lower jaw between an open condition and a closed condition, the upper jaw and the lower jaw operable in the closed condition to deliver RF energy to tissue,
   wherein one of the upper jaw and the lower jaw defines a second passage,
   wherein the electrosurgical device comprises an actuation wire looped through the second passage of said one of the upper jaw and the lower jaw,
   wherein the actuation wire comprises a first actuation wire section and a second actuation wire section, the first actuation wire section crossing over the second actuation wire section so that the first actuation wire section and the second actuation wire section exert equal forces on said one of the upper jaw and the lower jaw through which the actuation wire is looped.

2. The electrosurgical device of claim 1, wherein the upper jaw is pivotable relative to the lower jaw about a pivot point located adjacent to an outside edge of the upper jaw, the pivot point being offset from a center line of the device.

3. The electrosurgical device of claim 1, wherein the pivot connection comprises a semi-cylindrical element having a convex surface that engages a first side of the upper jaw.

4. The electrosurgical device of claim 3, wherein the pivot connection further comprises a concave surface that engages a second side of the upper jaw.

5. The electrosurgical device of claim 1 further comprising a lower jaw housing that contains the lower jaw, the lower jaw being positioned in a distal portion of the lower jaw housing.

6. The electrosurgical device of claim 5 further comprising a lower jaw pivot connection, wherein the lower jaw is pivotally connected to the lower jaw housing by the lower jaw pivot connection.

7. The electrosurgical device of claim 1 further comprising an elongated shaft and a wrist section between the elongated shaft and the upper and lower jaws, the upper and lower jaws being displaceable at the wrist section to allow the upper and lower jaws to bend relative to the elongated shaft.

8. The electrosurgical device of claim 7, further comprising a third passage defined in the wrist section, wherein the electrosurgical device further comprises an articulation wire looped through the third passage in the wrist section.

9. The electrosurgical device of claim 7, wherein the wrist section comprises a vertebra, a bushing and a self-straightening coupling between the vertebra and bushing to urge the upper and lower jaws toward a centered position.

10. The electrosurgical device of claim 1, wherein the upper jaw comprises a first mating surface and the lower jaw comprises a second mating surface that mates with the first mating surface, the first and second mating surfaces each comprising a V-shaped contour.

11. The electrosurgical device of claim 1, further comprising an articulation mechanism for controlling bending or turning motion of the upper and lower jaws.

12. The electrosurgical device of claim 11, wherein the articulation mechanism comprises a housing and an indexing disk rotatably displaceable in the housing.

13. The electrosurgical device of claim 12, wherein the articulation mechanism comprises an automatic locking mechanism that prevents external force on the upper and lower jaws from moving the upper and lower jaws out of an indexed position.

14. An electrosurgical device for cutting and sealing tissue, the electrosurgical device comprising:
an upper jaw located at a distal end of the electrosurgical device;
a lower jaw opposing the upper jaw;
a pivot connection that pivotally connects the upper jaw to the lower jaw;
a passage defined in one of the upper jaw and the lower jaw; and
an actuation wire looped through the passage in said one of the upper jaw and the lower jaw,
wherein the actuation wire comprises a first actuation wire section and a second actuation wire section, the first actuation wire section crossing over the second actuation wire section at a cross-over point so that the first actuation wire section and the second actuation wire section exert equal forces on said one of the upper jaw and the lower jaw through which the actuation wire is looped.

15. The electrosurgical device of claim 14, wherein the first and second actuation wire sections are twisted by 180° at the cross-over point.

16. The electrosurgical device of claim 14, wherein the first actuation wire section comprises a first arc length at the cross-over point, and the second actuation wire section comprises a second arc length at the cross-over point that is a mirror image of the first arc length, wherein the first arc length and the second arc length remain equal when the upper jaw and the lower jaw are articulated.

17. An electrosurgical device for cutting and sealing tissue, the electrosurgical device comprising:
an upper jaw located at a distal end of the electrosurgical device;
a lower jaw opposing the upper jaw;
a pivot connection that pivotally connects the upper jaw to the lower jaw;
an elongated shaft; and
a wrist mechanism between the elongated shaft and the upper and lower jaws,
wherein the upper and lower jaws are displaceable at the wrist mechanism to allow the upper and lower jaws to bend relative to the elongated shaft,
wherein the wrist mechanism comprises a wrist section, the wrist section comprising a vertebra and a bushing, wherein the vertebra and the bushing define a non-circular pivot interface formed between the vertebra and the bushing; and
wherein the wrist section comprises a self-straightening coupling between the vertebra and the bushing to urge the upper and lower jaws towards a centered position.

18. The electrosurgical device of claim 17, wherein the non-circular pivot interface comprises either a convex or concave mating surface being rounded on the vertebra and an opposing and matching concave or convex mating surface being rounded on the bushing.

19. The electrosurgical device of claim 17, wherein the non-circular pivot interface between the vertebra and the bushing has a parabolic geometry, a stepped geometry or a V-notched geometry, such that the vertebra and the bushing are nested when the wrist section is straight.

20. The electrosurgical device of claim 17, wherein one of the vertebra and the bushing comprises a convex mating surface, and the other of the vertebra and the bushing comprises a concave mating surface, the convex mating surface comprising a lobe extending outwardly, and the concave mating surface defining a recess extending into the concave mating surface, wherein the recess has a shape that conforms to the geometry of the lobe.

21. The electrosurgical device of claim 20, wherein, when the wrist section is straight, the convex mating surface and the lobe are in phase with the concave mating surface and the recess, and the lobe is nested in the recess.

22. The electrosurgical device of claim 21, wherein the convex mating surface and the lobe are shifted out of phase with the concave mating surface and the recess when the wrist section is articulated.

23. An electrosurgical device for cutting and sealing tissue, the electrosurgical device comprising:
an upper jaw located at a distal end of the electrosurgical device;
a lower jaw opposing the upper jaw;
a pivot connection that pivotally connects the upper jaw to the lower jaw; and an articulation mechanism for controlling bending or turning motion of the upper jaw and the lower jaw, wherein the articulation mechanism comprises a housing and an indexing disk arranged rotatably displaceable in the housing, wherein the housing comprises a plurality of ratchet notches and the indexing disk comprises an indexing arm for engaging the ratchet notches to index a position of the upper jaw and the lower jaw, wherein the articulation mechanism further comprises an automatic locking mechanism, wherein the automatic locking mechanism comprises a passive interlock mechanism preventing external force on the upper jaw and the lower jaw from moving the upper jaw and the lower jaw out of an indexed position.

24. The electrosurgical device of claim 23, wherein the articulation mechanism comprises an articulator being operable to rotate the indexing disk.

25. The electrosurgical device of claim 24, wherein the articulation mechanism includes a pair of indexing disks that hold the upper jaw and the lower jaw in an articulated position, and wherein each indexing disk has a pair of indexing arms.

26. The electrosurgical device of claim 25, wherein the ratchet notches are separated from one another by a plurality of ratchet teeth, and wherein the indexing arms are operable to engage and disengage the ratchet notches when the indexing disks are rotated in the housing.

27. The electrosurgical device of claim 25, wherein the articulation mechanism comprises a pair of projections, and the articulation mechanism comprises a centering mechanism, the centering mechanism comprising a pair of leaf springs extending from each indexing disk and having a distal end that is held in a captive position between the pair of projections, the centering mechanism exerting a centering force and biasing the articulation mechanism to a centered condition.

28. The electrosurgical device of claim 25, wherein the automatic locking mechanism includes a plurality of detents on the articulation mechanism, each detent being movable with respect to the indexing disks between a locking position and a release position.

29. The electrosurgical device of claim 27, wherein the articulation mechanism has a pair of handles extending outwardly from the indexing disks, and wherein the upper jaw and the lower jaw are articulated by exerting a rotation force on the handles, wherein the rotation force is opposed by the centering force.

30. The electrosurgical device of claim 29, wherein the articulation mechanism rotates relative to the indexing disk and thus the detents move out of the locking position to the release position when the rotation force is greater than the centering force.

31. The electrosurgical device according to claim 29, wherein the articulation mechanism has a plurality of abutment edges, and the indexing disks have corresponding abutment edges, wherein the abutment edges of the articulation mechanism and the abutment edges of the indexing disks approach and contact each other when the rotation force is applied to the handles of the articulation mechanism, wherein the indexing disks and the articulation mechanism rotate in tandem with each other when the abutment edges of the articulation mechanism are in contact with the abutment edges of the indexing disks.

* * * * *